United States Patent
Heidecke et al.

(10) Patent No.: US 10,739,346 B2
(45) Date of Patent: Aug. 11, 2020

(54) DIAGNOSIS OF CANCER BY DETECTING AUTO-ANTIBODIES AGAINST EGF-RECEPTOR

(71) Applicant: CELLTREND GMBH, Luckenwalde (DE)

(72) Inventors: Harald Heidecke, Berlin (DE); Kai Schulze-Forster, Berlin (DE)

(73) Assignee: CELLTREND GMBH, Luckenwalde (DE)

( * ) Notice: Subject to any disclaimer, the term of this patent is extended or adjusted under 35 U.S.C. 154(b) by 145 days.

(21) Appl. No.: 15/116,468

(22) PCT Filed: Feb. 3, 2015

(86) PCT No.: PCT/EP2015/052181
§ 371 (c)(1),
(2) Date: Aug. 3, 2016

(87) PCT Pub. No.: WO2015/117951
PCT Pub. Date: Aug. 13, 2015

(65) Prior Publication Data
US 2017/0010271 A1    Jan. 12, 2017

(30) Foreign Application Priority Data
Feb. 4, 2014 (EP) .................................. 14153820

(51) Int. Cl.
| | | |
|---|---|---|
| G01N 33/574 | (2006.01) | |
| G01N 33/564 | (2006.01) | |
| G01N 33/74 | (2006.01) | |
| C07K 16/28 | (2006.01) | |
| A61K 39/00 | (2006.01) | |

(52) U.S. Cl.
CPC ... G01N 33/57449 (2013.01); C07K 16/2863 (2013.01); G01N 33/564 (2013.01); G01N 33/57488 (2013.01); G01N 33/74 (2013.01); A61K 2039/505 (2013.01); C07K 2317/24 (2013.01); C07K 2317/76 (2013.01); G01N 2333/485 (2013.01); G01N 2333/71 (2013.01); G01N 2800/52 (2013.01); G01N 2800/54 (2013.01)

(58) Field of Classification Search
None
See application file for complete search history.

(56) References Cited

U.S. PATENT DOCUMENTS

| | | | |
|---|---|---|---|
| 7,732,157 B1 | 6/2010 | Baron et al. | |
| 2008/0213921 A1* | 9/2008 | Robertson | G01N 33/54393 436/536 |
| 2009/0017050 A1* | 1/2009 | Powell | C07K 16/2863 424/184.1 |

FOREIGN PATENT DOCUMENTS

| | | |
|---|---|---|
| WO | 2005043165 A2 | 5/2005 |
| WO | 2008032084 A1 | 3/2008 |
| WO | 2008061104 A2 | 5/2008 |
| WO | 2011073905 A1 | 6/2011 |
| WO | 2012113061 A1 | 8/2012 |
| WO | 2013182537 A1 | 12/2013 |

OTHER PUBLICATIONS

Olsen et al. (Clin. Chem. Lab Met. 51(12): 2325-2329, Dec. 2013).*
Wilken et al. EGFR/HER-targeted therapeutics in ovarian cancer. Future Med Chem. 4(4): 447-469, Mar. 2012. Presented herein as pp. 1-39.*
US, 371 U.S. Appl. No. 15/116,476 of PCT/EP2015/052182, filed Aug. 3, 2016, Harald Heidecke.
Scambia et al; Epidermal growth factor, oestrogen and progesterone receptor expression in primary ovarian cancer; correlation with clinical outcome and response to chemotherapy, British Journal of CA, Nature Pub. Group, GB, vol. 72, No. 2, Jan. 1, 1995 (Jan. 1, 1995), pp. 36-366, XP009113999, ISSN: 007-0920.
EP 15702480.3 Office Action dated Jul. 12, 2017 (6 pgs.).
Li, et al., "Detecting EGFR Autoantibodies in Serums of NSCLC Patients with Peptide Array", EBSCO Information Services, Chinese Journal of Lung Cancer, Jul. 2010, vol. 13 Issue 7, pp. 727-730, 4p. 1 Color Photograph (with English Abstract).
Written Opinion of the International Searching Authority dated Apr. 22, 2015 for International Application No. PCT/EP2015/052181, filed on Feb. 3, 2015 and published as WO 2015/117951 A1 on Aug. 13, 2015 (Applicant—CELLTREND GMBH // Inventors Heidecke, et al.) (6 pgs.).

\* cited by examiner

*Primary Examiner* — Alana Harris Dent
(74) *Attorney, Agent, or Firm* — Morris, Manning & Martin, LLP; Daniel E. Sineway, Esq.; Adam J. Thompson, Esq.

(57) ABSTRACT

The present invention relates to a method for diagnosis of a cancer, comprising the steps of (i) determining the level of antibodies against epidermal growth factor receptor (EGFR) in a sample from a subject to be diagnosed, (ii) comparing the determined level in the sample to a control level derived from subjects without cancer; wherein a decreased level in the sample from the subject to be diagnosed as compared to the control level is indicative for cancer in the subject. Furthermore, the invention relates to method of predicting response and outcome of a treatment of a cancer with an inhibitor of EGFR activity.

13 Claims, 11 Drawing Sheets

Specification includes a Sequence Listing.

A

B

C

SEQUENCE LISTING

```
<160> NUMBER OF SEQ ID NOS: 1

<210> SEQ ID NO 1
<211> LENGTH: 1210
<212> TYPE: PRT
<213> ORGANISM: Homo sapiens
<220> FEATURE:
<223> OTHER INFORMATION: Amino acid sequence of the human EGF-receptor

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125
```

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
            165                 170                 175

Ser Met Asp Phe Gln Asn His Leu Gly Ser Cys Gln Lys Cys Asp Pro
        180                 185                 190

Ser Cys Pro Asn Gly Ser Cys Trp Gly Ala Gly Glu Glu Asn Cys Gln
    195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
            245                 250                 255

Glu Ala Thr Cys Lys Asp Thr Cys Pro Pro Leu Met Leu Tyr Asn Pro
        260                 265                 270

Thr Thr Tyr Gln Met Asp Val Asn Pro Glu Gly Lys Tyr Ser Phe Gly
    275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
            325                 330                 335

Cys Asn Gly Ile Gly Ile Gly Glu Phe Lys Asp Ser Leu Ser Ile Asn
        340                 345                 350

Ala Thr Asn Ile Lys His Phe Lys Asn Cys Thr Ser Ile Ser Gly Asp
    355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
            405                 410                 415

Leu His Ala Phe Glu Asn Leu Glu Ile Ile Arg Gly Arg Thr Lys Gln
        420                 425                 430

His Gly Gln Phe Ser Leu Ala Val Val Ser Leu Asn Ile Thr Ser Leu
    435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
            485                 490                 495

Asn Ser Cys Lys Ala Thr Gly Gln Val Cys His Ala Leu Cys Ser Pro
        500                 505                 510

Glu Gly Cys Trp Gly Pro Glu Pro Arg Asp Cys Val Ser Cys Arg Asn
    515                 520                 525

Val Ser Arg Gly Arg Glu Cys Val Asp Lys Cys Asn Leu Leu Glu Gly
530                 535                 540

-continued

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
                660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln

-continued

```
                965                 970                 975
Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe Phe
    1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
                1045                1050                1055

Ser Cys Pro Ile Lys Glu Asp Ser Phe Leu Gln Arg Tyr Ser Ser Asp
                1060                1065                1070

Pro Thr Gly Ala Leu Thr Glu Asp Ser Ile Asp Asp Thr Phe Leu Pro
            1075                1080                1085

Val Pro Glu Tyr Ile Asn Gln Ser Val Pro Lys Arg Pro Ala Gly Ser
    1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
                1125                1130                1135

Glu Tyr Leu Asn Thr Val Gln Pro Thr Cys Val Asn Ser Thr Phe Asp
            1140                1145                1150

Ser Pro Ala His Trp Ala Gln Lys Gly Ser His Gln Ile Ser Leu Asp
            1155                1160                1165

Asn Pro Asp Tyr Gln Gln Asp Phe Phe Pro Lys Glu Ala Lys Pro Asn
    1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
            1205                1210
```

DIAGNOSIS OF CANCER BY DETECTING AUTO-ANTIBODIES AGAINST EGF-RECEPTOR

CROSS-REFERENCE TO RELATED APPLICATIONS

This application is a national stage application under 35 U.S.C. § 371, and claims priority to and the benefit of the filing date of International Application Number PCT/EP2015/052181, filed Feb. 3, 2015, which is herein incorporated in its entirety.

REFERENCE TO A SEQUENCE LISTING SUBMITTED AS A TEXT FILE VIA EFS-WEB

The Sequence Listing submitted Aug. 3, 2016 as a text file named "31904_111942_1U1_SeqListing.txt", created on Aug. 3, 2016, and having size of 12,288 bytes is hereby incorporated by reference pursuant to 37 C.F.R. § 1.52(e)(5).

FIELD OF THE INVENTION

The present invention is in the field of diagnostics, prognosis and therapeutics for cancer, more in particular in the field of diagnosis and therapy of epithelial cancer, more particular in the field of diagnosis, prognosis and therapy of ovarian cancer.

BACKGROUND OF THE INVENTION

According to the American Cancer Society ovarian cancer is expected to account for over 22,000 new cancer diagnoses and more than 14,000 deaths in 2013 in the US alone. Of the gynecologic malignancies, ovarian cancer has the highest mortality rate. In early stages of the disease, ovarian cancer is nearly asymptomatic. Hence, a large portion of the patients present with clinically advanced stages of ovarian cancer. However, the 5-year survival rate for patients diagnosed with early-stage disease is often>90%, but it is<20% for advanced-stage disease, underscoring the importance of early detection.

Current diagnosis of ovarian cancer relies on pelvic exam, transvaginal ultrasonography, (TVS), abdominal ultrasonography, and exploratory or diagnostic laparoscopy. The most commonly used biomarker for clinical screening and prognosis in patients with ovarian cancer is ovarian cancer antigen 125 (CA125) (Coticchia et al. (2008), J. Natl. Compr. Canc. Netw. 6(8):795-802). Serum CA125 levels are elevated in ≈80% of patients with advanced-stage epithelial ovarian cancer but are increased in only 50-60% of patients with early-stage disease. Serum CA125 levels may be falsely elevated in women with any i.p. pathology resulting in irritation of the serosa of the peritoneum or pericardium, uterine fibroids, renal disorders, and normal menses. Moreover, serum CA125 levels do not predict the outcome of cytoreductive surgery in patients with advanced epithelial ovarian cancer. Further biomarkers include, for example, Human Epidymis Protein 4 (HE4) and Mesothelin (Sarojini et al. (2012), Journal of Oncology 102, Article ID 709049). Severeness of ovarian cancer is categorized by the grade and stage of tumorization. This nowadays can only be performed by evaluation of the tumors under or after surgical treatment or by combining marker evaluation and (histological) evaluation of tissue. Staging is very important because ovarian cancers have different prognosis at different stages and may be treated differently. The accuracy of the staging may determine whether or not a patient will be cured. If the cancer isn't accurately staged, then cancer that has spread outside the ovary might be missed and not treated. Once a stage has been given it does not change, even when the cancer comes back or spreads to new locations in the body.

Ovarian cancer staging is by FIGO staging system uses information obtained after surgery, which can include a total abdominal hysterectomy, removal of (usually) both ovaries and fallopian tubes, (usually) the omentum, and pelvic (peritoneal) washings for cytopathology. The AJCC stage is the same as the FIGO stage. The AJCC staging system describes the extent of the primary tumor (T), the absence or presence of metastasis to nearby lymph Nodes (N), and the absence or presence of distant Metastasis (M).

| | |
|---|---|
| Stage I | limited to one or both ovaries |
| IA | involves one ovary; capsule intact; no tumor on ovarian surface; no malignant cells in ascites or peritoneal washings |
| IB | involves both ovaries; capsule intact; no tumor on ovarian surface; negative washings |
| IC | tumor limited to ovaries with any of the following: capsule ruptured, tumor on ovarian surface, positive washings |
| Stage II | pelvic extension or implants |
| IIA | extension or implants onto uterus or fallopian tube; negative washings |
| IIB | extension or implants onto other pelvic structures; negative washings |
| IIC | pelvic extension or implants with positive peritoneal washings |
| Stage III | peritoneal implants outside of the pelvis; or limited to the pelvis with extension to the small bowel or omentum |
| IIIA | microscopic peritoneal metastases beyond pelvis |
| IIIB | macroscopic peritoneal metastases beyond pelvis less than 2 cm in size |
| IIIC | peritoneal metastases beyond pelvis >2 cm or lymph node metastases |
| Stage IV | distant metastases to the liver or outside the peritoneal cavity |

Para-aortic lymph node metastases are considered regional lymph nodes (Stage IIIC). As there is only one para-aortic lymph node intervening before the thoracic duct on the right side of the body, the ovarian cancer can rapidly spread to distant sites such as the lung.

The AJCC/TNM staging system includes three categories for ovarian cancer, T, N and M. The T category contains three other subcategories, T1, T2 and T3, each of them being classified according to the place where the tumor has developed (in one or both ovaries, inside or outside the ovary). The T1 category of ovarian cancer describes ovarian tumors that are confined to the ovaries, and which may affect one or both of them. The sub-subcategory T1a is used to stage cancer that is found in only one ovary, which has left the capsule intact and which cannot be found in the fluid taken from the pelvis. Cancer that has not affected the capsule, is confined to the inside of the ovaries and cannot be found in the fluid taken from the pelvis but has affected both ovaries is staged as T1b. T1c category describes a type of tumor that can affect one or both ovaries, and which has grown through the capsule of an ovary or it is present in the fluid taken from the pelvis. T2 is a more advanced stage of cancer. In this case, the tumor has grown in one or both ovaries and is spread to the uterus, fallopian tubes or other pelvic tissues. Stage T2a is used to describe a cancerous tumor that has spread to the uterus or the fallopian tubes (or both) but which is not present in the fluid taken from the pelvis. Stages T2b and T2c indicate cancer that metastasized to other pelvic tissues than the uterus and fallopian tubes and which cannot be seen in the fluid taken from the pelvis, respectively tumors that spread to any of the pelvic tissues (including uterus and fallopian tubes) but which can also be found in the fluid taken from the pelvis. T3 is the stage used to describe cancer that has spread to the peritoneum. This stage provides information on the size of the metastatic tumors (tumors that are located in other areas of the body, but are caused by ovarian cancer). These tumors can be very small, visible only under the microscope (T3a), visible but not larger than 2 centimeters (T3b) and bigger than 2 centimeters (T3c). This staging system also uses N categories to describe cancers that have or not spread to nearby lymph nodes. There are only two N categories, N0 which indicates that the cancerous tumors have not affected the lymph nodes, and N1 which indicates the involvement of lymph nodes close to the tumor. The M categories in the AJCC/TNM staging system provide information on whether the ovarian cancer has metastasized to distant organs such as liver or lungs. M0 indicates that the cancer did not spread to distant organs and M1 category is used for cancer that has spread to other organs of the body.

The AJCC/TNM staging system also contains a Tx and a Nx sub-category which indicates that the extent of the tumor cannot be described because of insufficient data, respectively the involvement of the lymph nodes cannot be described because of the same reason. The ovarian cancer stages are made up by combining the TNM categories in the following manner:

Stage I: T1+N0+M0; IA: T1a+N0+M0; IB: T1b+N0+M0; IC: T1c+N0+M0;
Stage II: T2+N0+M0; IIa: T2a+N0+M0; IIB: T2b+N0+M0; IIC: T2c+N0+M0;
Stage III: T3+N0+M0; IIIA: T3a+N0+M0; IIIB: T3b+N0+M0; III C: T3c+N0+M0 or Any T+N1+M0;
Stage IV: Any T+Any N+M1

In addition to being staged, like all cancers ovarian cancer is also graded. The histologic grade of a tumor measures how abnormal or malignant its cells look under the microscope. There are four grades indicating the likelihood of the cancer to spread and the higher the grade, the more likely for this to occur. Grade 0 is used to describe non-invasive tumors. Grade 0 cancers are also referred to as borderline tumors. Grade 1 tumors have cells that are well differentiated (look very similar to the normal tissue) and are the ones with the best prognosis. Grade 2 tumors are also called moderately well differentiated and they are made up by cells that resemble the normal tissue. Grade 3 tumors have the worst prognosis and their cells are abnormal, referred to as poorly differentiated.

However, there is a need for improved tools for the early detection; staging, grading and prognosis of ovarian cancer.

SUMMARY OF THE INVENTION

Subject of the invention is a method for diagnosis of a cancer, comprising the steps of
(i) determining the level of antibodies against epidermal growth factor receptor (EGFR) in a sample from a subject to be diagnosed,
(ii) comparing the determined level in the sample to a control level derived from subjects without cancer;
wherein a decreased level in the sample from the subject to be diagnosed as compared to the control level is indicative for cancer in the subject.

The present invention is based on the finding of that levels of autoimmuno-antibodies in subjects have diagnostic and predictive properties. The to be detected in connection with the present invention are therefore autoantibody, i.e. those produced by immunesystem of the subject to be diagnosed or being or to be treated.

The invention further pertains to a method for diagnosis of a cancer, wherein the level of antibodies against epidermal growth factor receptor (EGFR) is determined in a sample from a subject to be diagnosed and wherein a level of anti-EGFR antibodies below 50 units/ml is indicative for cancer, preferably a level below 40 units/ml, even more preferred below 30 units/ml, in a further preferred embodiment a level of anti-EGFR antibodies below 25 units/ml is indicative for cancer.

The present invention is further directed to an immunoassay method for detecting an anti-EGFR antibody in a sample from a subject, comprising the steps of
(a) contacting the sample suspected of comprising an anti-EGFR antibody with epidermal growth factor receptor (EGFR) or an antigenic peptide fragment thereof under conditions allowing for the formation of a complex between the anti-EGFR antibody with EGFR or the peptide fragment thereof,
(b) detecting the complex.

In the context of the present invention EGFR or an antigenic peptide fragment thereof can thus be used for the diagnosis of cancer.

The present invention further relates to a research and/or diagnostic kit for the diagnosis of cancer or for the prediction of response or non-response in a patient, wherein the kit comprises epidermal growth factor receptor (EGFR) or an antigenic peptide fragment thereof The inventors also found that the level of antibodies against epidermal growth factor receptor (EGFR) correlates with the risk of relapse or mortality in subjects treated for cancer. Decreased levels of anti-EGFR antibodies in samples correlated with a higher risk of relapse and/or mortality in patients treated for cancer. Hence, levels of anti-EGFR antibodies in samples of patients to be treated are an indicator for response or non-response of a patient, i.e. whether improvement of the disease is achieved in a patient (responder) or not (non-responder). If a patient responds to a treatment the disease is ameliorated. It might be the case that a patient responds to a treatment at first but suffers from relapse of the disease at a later stage. Also this is a form of non-response. However, it is difficult to predict whether a patient will respond or not to a treatment as it may be determined only at later stages with the known methods, e.g. when relapse, progression or death occurs. This problem is solved by the present invention as it provides a predictive method to predict whether a subject will respond or not to a certain treatment, e.g. a treatment with an angiogenesis inhibitor.

Therefore, the invention also relates to a method for determining whether a subject being treated or to be treated for cancer will respond to said treatment comprising the steps of
(i) determining the level of antibodies against epidermal growth factor receptor (EGFR) in a sample from said subject being treated or to be treated, and
(ii) comparing the determined level in the sample to either one or both of a first and second EGFR antibody control level, wherein
  a) the first EGFR antibody control level is derived from subjects responding to said treatment, and
  b) the second EGFR antibody control level is derived from a subject not responding to said treatment,
wherein a decreased level in the sample from the subject being treated or to be treated as compared to the first EGFR antibody control level and/or an equal level as compared to the second EGFR antibody control level is indicative for a non-response of said subject to said treatment, and wherein an increased level in the sample from the subject being treated or to be treated as compared to the second EGFR antibody control level and/or an equal level as compared to the first EGFR antibody control level is indicative for a response of said subject to said treatment. In a preferred embodiment of the invention the subject is to be treated, i.e. the method to determine response of a subject is performed before the onset of treatment. In a preferred embodiment the treatment for cancer comprises the administration of a drug. In a further preferred embodiment the treatment comprises surgical removal of the tumor and administration of a drug. In a preferred embodiment said drug is a chemotherapeutic drug or an EGF-receptor inhibitor. A preferred chemotherapeutic drug is a platinum analog, preferably selected from the group consisting of cisplatin, carboplatin, oxaliplatin, satraplatin, and triplatin-tetranitrate, preferably cisplatin or carboplatin. Preferred EGF-receptor inhibitor is selected from the group consisting of panitumumab, gefitinib, erlotinib, cetuximab, lapatinib, vandetanib, trastuzumab, zalutumumab, nimotuzumab, and matuzumab, preferably panitumumab. Therefore, in one embodiment the invention also relates to a method for determining whether a subject being treated or to be treated for cancer with chemotherapeutic drug and by surgery will respond to said treatment comprising the steps of (i) determining the level of antibodies against epidermal growth factor receptor (EGFR) in a sample from said subject being treated or to be treated, and (ii) comparing the determined level in the sample to either one or both of a first and second EGFR antibody control level, wherein a) the first EGFR antibody control level is derived from subjects responding to said treatment, and b) the second EGFR antibody control level is derived from a subject not responding to said treatment, wherein a decreased level in the sample from the subject being treated or to be treated as compared to the first EGFR antibody control level is indicative for a non-response of said subject to said treatment, and wherein an increased level in the sample from the subject being treated or to be treated as compared to the second EGFR antibody control level is indicative for a response of said subject to said treatment.

The present invention also relates to a method of treating cancer in a subject, comprising determining the level of antibodies against epidermal growth factor receptor (EGFR) in a sample from the subject, wherein when the level of anti-EGFR antibodies in a sample from the subject is above 10.0 units/ml, the subject is treated, preferably above 20 units/ml, more preferred above 30 units/ml, further preferred above 40 units/ml. In a particular embodiment the patient is treated at levels of EGFR antibodies above 34 units/ml. In one embodiment the treatment comprises administration of a drug. In a preferred embodiment said drug is a chemotherapeutic drug or an inhibitor of EGFR activity, e.g. an EGF inhibitor, or an EGFR inhibitor. A preferred chemotherapeutic drug is a platinum analog. One preferred EGF-receptor inhibitor is panitumumab. The skilled person knows that in some cases surgical removal before onset of application of the drug is necessary. In such case, the level of EGFR antibodies in the sample of the patient is preferably measured after surgical removal of the tumor, but preferably before onset of the treatment by the drug.

As outlined, results of non-response of a patient to a treatment may be relapse of cancer, death (mortality) or progression of the cancer. Hence, in a preferred embodiment of the method to determine/predict the response of a subject to a treatment the present invention also relates to a method for the prediction of risk stratification for relapse of cancer and/or mortality in a patient being treated or to be treated with a drug, the method comprising the steps of (i) determining the level of antibodies against epidermal growth factor receptor (EGFR) in a sample from said subject being treated or to be treated for cancer with a drug (ii) comparing the determined level in the sample to either one or both of a first and a second EGFR antibody control level, a) wherein the first EGFR antibody control level is derived from subjects not showing relapse of cancer or mortality after treatment with said drug, and b) wherein the second EGFR antibody control level is derived from subjects showing relapse of cancer or mortality after treatment with said drug, wherein a decreased level in the sample from the subject being treated as compared to the first EGFR antibody control level and/or an equal level as compared to the second EGFR antibody control level is indicative for relapse and/or mortality in the subject, and wherein an increased level in the sample from the subject being treated as compared to the second EGFR antibody control level and/or an equal level as compared to the first EGFR antibody control level is indicative for no relapse and/or no mortality in the subject. Preferably the level in said patient is determined before the onset of treatment. In a preferred embodiment of the present invention the first EGFR antibody control level is derived from subjects that did not show relapse or progression of cancer or mortality within 24 months after onset of treatment with said drug and the second EGFR antibody control level is derived from subjects that did show relapse or progression of cancer or mortality within 24 months after onset of treatment with said drug.

The present invention also relates to a method prediction of risk stratification for relapse of cancer and/or mortality in a patient being treated or to be treated with a drug, comprising determining the level of antibodies against epidermal growth factor receptor (EGFR) in a sample from the subject, wherein when the level of anti-EGFR antibodies in a sample from the subject is below 30 units/ml, preferably below 29 units/ml, more preferred below 28 units/ml, further preferred below 25 units/ml., is indicative for relapse or progression of cancer or mortality in the subject, preferably a level of anti-EGFR antibodies below 29 units/ml, more preferred below 28 units/ml, further preferred below 25 units/ml, is indicative for relapse or progression of cancer or mortality in the subject.

As will be readily understood by the skilled person, this method may be performed as a method for monitoring treatment efficiency. In this embodiment the levels of anti-EGFR antibodies in said subject is determined during treatment, i.e. in a subject being treated with said drug.

DETAILED DESCRIPTION OF THE INVENTION

The present invention is based on the surprising finding of the inventors that in samples of patients with cancer decreased levels of anti-EGFR antibodies can be found as compared to subjects without cancer. In other words the inventors have found that patients with ovarian cancer have little or no detectable antibodies against epidermal growth factor receptor (EGFR) in the blood (e.g determined in the serum) whereas in control groups anti-EGFR auto-antibodies can be detected at higher levels.

The invention relates to a method for the diagnosis of a cancer, comprising the steps of
(i) determining the level of antibodies against EGFR in a sample from a subject to be diagnosed,
(ii) comparing the determined level in the sample to a control level derived from subjects without cancer;
wherein a decreased level in the sample from the subject to be diagnosed as compared to the control level is indicative for cancer in the subject.

Figure 1:
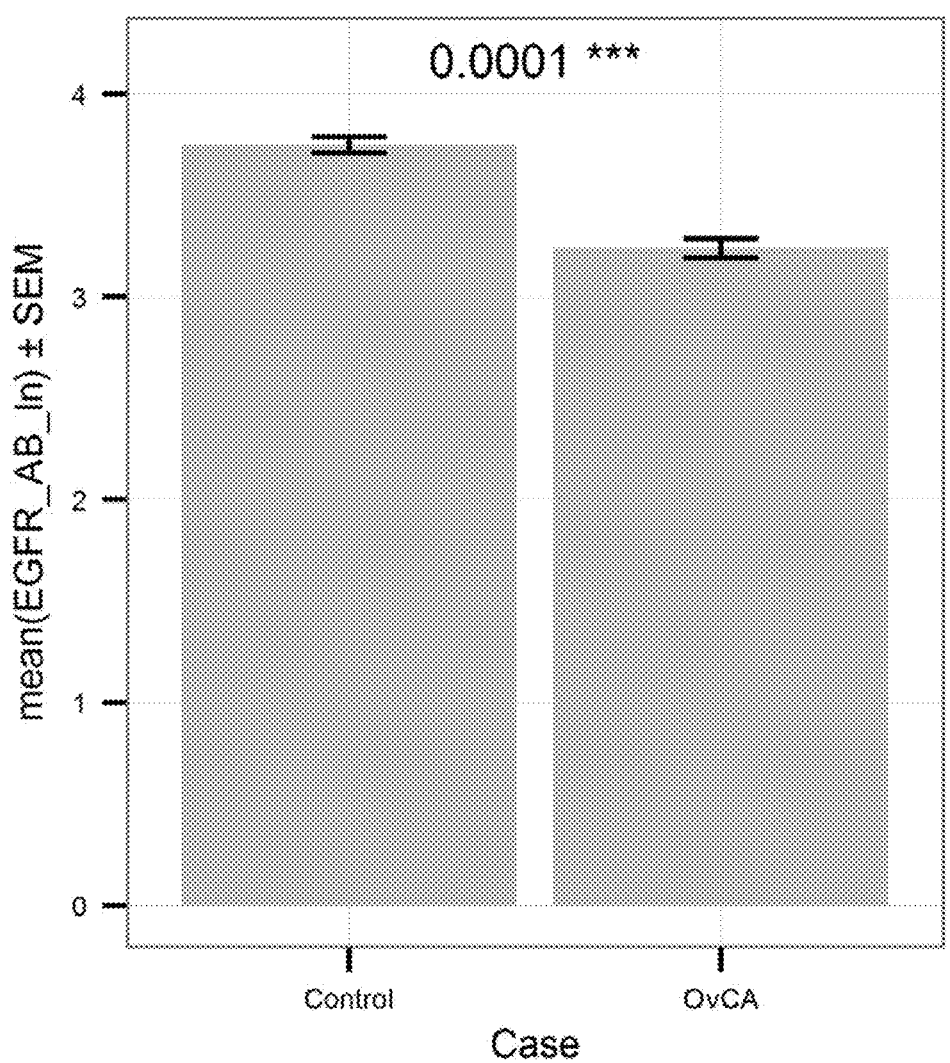
FIG. 1: Comparison of the mean level of anti-EGFR antibodies (ln of units/ml) in serum samples of ovarian cancer patients (OvCA; ln of mean 3.238; n=201) to the mean level of anti-EGFR antibodies in serum samples of a healthy control group (Control, ln of mean=3.749; n=131). The p-value is indicated on top. Bars indicate standard error of mean.

As can be derived from FIG. 1, the ln of the mean level of EGFR antibodies in patients suffering from ovarian cancer is 3.238 (=25.5 units) and in healthy subjects 3.749 (=42.5 units). Hence, in one embodiment a level of less than 0.9 fold as compared to the control level from subjects without cancer is indicative for the presence of cancer, preferably a level of less than 0.8 fold, more preferably of less than 0.7 fold, even more preferred of less than 0.65 fold. The cancer is preferably an EGF or EGFR driven cancer as defined herein.

Particularly preferred is ovarian cancer. The skilled person will acknowledge that in case a certain cancer is to be diagnosed, the control level is preferably derived from subjects not having this particular cancer.

Auto-antibodies directed against EGFR are not known until today. The inventors of the present application for the first time demonstrate the presence of such antibodies as well as the diagnostic and predictive value. It was found that a decrease in the level of antibodies directed against EGFR in samples of a subject to be diagnosed as compared samples from subjects with proven absence of cancer is indicative for the presence of cancer as well as for the prediction of response or non-response to a treatment of the cancer with a drug or surgical removal and subsequent treatment with a drug. Hence, "cancer" in connection with the present invention is to be understood as any diseases involving unregulated cell growth. Cancer in this regard is a disease where cells divide and grow uncontrollably resulting in the formation of malignant tumors. However, in a preferred embodiment of the present invention "cancer" refers to an EGFR or EGF associated cancer. EGFR and EGF associated cancers are known by the skilled person. Mutations that lead to EGFR overexpression (known as upregulation) or overactivity have been associated with a number of cancers, including lung cancer, anal cancers (Walker F, Abramowitz L, Benabderrahmane D, Duval X, Descatoire V, Hénin D, Lehy T, Aparicio T (November 2009). "Growth factor receptor expression in anal squamous lesions: modifications associated with oncogenic human papillomavirus and human immunodeficiency virus". Hum. Pathol. 40 (11): 1517-27), ovarian cancer and glioblastoma multiforme. Mutations involving EGFR could lead to its constant activation, which could result in uncontrolled cell division—a predisposition for cancer (Lynch T J, Bell D W, Sordella R, Gurubhagavatula S, Okimoto R A, Brannigan B W, Harris P L, Haserlat S M, Supko J G, Haluska F G, Louis D N, Christiani D C, Settleman J, Haber D A (May 2004). "Activating mutations in the epidermal growth factor receptor underlying responsiveness of non-small-cell lung cancer to gefitinib". N. Engl. J. Med. 350 (21): 2129-39). Mutations, amplifications or misregulations of EGFR or family members are implicated in about 30% of all epithelial cancers. Hence, in a preferred embodiment of the present invention the cancer is an epithelial cancer, preferably selected from the group consisting of breast cancer, lung cancer, colon cancer, renal cancer, a glioblastoma and ovarian cancer. In a particularly preferred embodiment the cancer according to the present invention, including all embodiments, is an ovarian cancer. Ovarian cancer often derives from the epithelium of the ovary, but may also be derived from fallopian tube. However, it was found that in both cases the method of the present invention is predictive for the presence of cancer or the response to a certain treatment. Hence, in one embodiment of the present invention cancer is an ovarian cancer, the ovarian cancer being epithelial ovarian cancer or cancer derived from the fallopian tube.

The skilled person knows that depending on the subject, different cancers may be diagnosed. He is aware that he also may have to consider further parameters to diagnose the subject, e.g. when diagnosing ovarian cancer, the subject has to be female. In the context of the present invention the subject to be diagnosed is a mammal, preferably a human. In a further preferred embodiment the subject is a female mammal, preferably a female human subject suspected of having ovarian cancer or a female mammal, preferably a female human subject to be screened for the presence of ovarian cancer, preferably a female human subject to be treated or being treated for ovarian cancer with a drug.

The invention particularly relates to a method for diagnosis of ovarian cancer, wherein the level of antibodies against EGFR is determined in a sample from a subject to be diagnosed and wherein a level of anti-EGFR antibodies below 50 units/ml is indicative for ovarian cancer, preferably a level below 40 units/ml, even more preferred below 30 units/ml, in a further preferred embodiment a level of anti-EGFR antibodies below 25 units/ml is indicative for cancer.

In the context of the present invention the terms "EGFR" and "EGF-receptor" equally relate to the "epithelial growth factor receptor" (also known as"ErbB-1" and HER1).

The epidermal growth factor receptor is a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4). Mutations affecting EGFR expression or activity could result in cancer (Zhang H, Berezov A, Wang Q, Zhang G, Drebin J, Murali R, Greene M I (August 2007). "ErbB receptors: from oncogenes to targeted cancer therapies". J. Clin. Invest. 117 (8): 2051-8).

EGFR (epidermal growth factor receptor) exists on the cell surface and is activated by binding of its specific ligands, including epidermal growth factor and transforming growth factor α (TGFα). ErbB2 has no known direct activating ligand, and may be in an activated state constitutively or become active upon heterodimerization with other family members such as EGFR. Upon activation by its growth factor ligands, EGFR undergoes a transition from an inactive monomeric form to an active homodimer (Yosef Yarden and Joseph Schlessinger (1987). "Epidermal Growth-Factor Induces Rapid, Reversible Aggregation of the Purified Epidermal Growth-Factor Receptor". Biochemistry 26 (5): 1443-1451). In addition to forming homodimers after ligand binding, EGFR may pair with another member of the ErbB receptor family, such as ErbB2/Her2/neu, to create an activated heterodimer. Formation of clusters of activated EGFRs have been reported, although it remains unclear whether this clustering is important for activation itself or if it is a secondary effect occurring after activation by dimerization.

EGFR dimerization stimulates its intrinsic intracellular protein-tyrosine kinase activity and autophosphorylation of tyrosine (Y) residues in the C-terminal domain of EGFR occurs, e.g. Y992, Y1045, Y1068, Y1148 and Y1173 (Downward J, Parker P, Waterfield Md. (1984). "Autophosphorylation sites on the epidermal growth factor receptor". Nature 311 (5985): 483-5). Thereby downstream activation and signaling is activated by binding of other proteins to the phosphorylated tyrosines through their phosphotyrosine-binding SH2 domains. These downstream signaling proteins initiate several signal transduction cascades, principally the MAPK, Akt and JNK pathways, leading to DNA synthesis and cell proliferation (Oda K, Matsuoka Y, Funahashi A, Kitano H (2005). "A comprehensive pathway map of epidermal growth factor receptor signaling". Mol. Syst. Biol. 1 (1): 2005.0010). Such proteins modulate phenotypes such as cell migration, adhesion, and proliferation. Activation of the receptor is important for the innate immune response in human skin. The kinase domain of EGFR can also cross-phosphorylate tyrosine residues of other receptors it is aggregated with, and can itself be activated in that manner.

The identification of EGFR as an oncogene has led to the development of anticancer therapeutics directed against EGFR, including gefitinib (Paez J G, Janne P A, Lee J C, Tracy S, Greulich H, Gabriel S, Herman P, Kaye F J, Lindeman N, Boggon T J, Naoki K, Sasaki H, Fujii Y, Eck M J, Sellers W R, Johnson B E, Meyerson M' (June 2004). "EGFR mutations in lung cancer: correlation with clinical response to gefitinib therapy". Science 304 (5676): 1497-500), erlotinib, and cetuximab. Most of the therapeutic approaches target the misregulation of EGFR, i.e. inhibit EGFR activation. Cetuximab and panitumumab are examples of monoclonal antibody inhibitors used for treatment. Other monoclonal antibodies in clinical development are zalutumumab, nimotuzumab, and matuzumab. The monoclonal antibodies block the extracellular ligand binding domain. With the binding site blocked, signal molecules can no longer attach there and activate the tyrosine kinase.

Another method is using small molecules to inhibit the EGFR tyrosine kinase domain at the intracellular part. Without kinase activity, EGFR is unable to activate itself, which is a prerequisite for binding of downstream adaptor proteins. Ostensibly by halting the signaling cascade in cells that rely on this pathway for growth, tumor proliferation and migration is diminished. Gefitinib, erlotinib, and lapatinib (mixed EGFR and ERBB2 inhibitor) are examples of small molecule kinase inhibitors. There are several quantitative methods available that use protein phosphorylation detection to identify EGFR family inhibitors (Olive D M (October 2004). "Quantitative methods for the analysis of protein phosphorylation in drug development". Expert Rev Proteomics 1 (3): 327-41).New drugs such as gefitinib and erlotinib directly target the EGFR. Patients have been divided into EGFR-positive and EGFR-negative, based upon whether a tissue test shows a mutation. EGFR-positive patients have shown a 60% response rate, which exceeds the response rate for conventional chemotherapy. However, clear prediction of the response of a patient to a treatment is still an issue (Jackman D M, Miller V A, Cioffredi L A, Yeap B Y, Janne P A, Riely G J, Ruiz M G, Giaccone G, Sequist L V, Johnson B E (August 2009). "Impact of epidermal growth factor receptor and KRAS mutations on clinical outcomes in previously untreated non-small cell lung cancer patients: results of an online tumor registry of clinical trials". Clin. Cancer Res. 15 (16): 5267-73). Many patients develop resistance increasing the risk for relapse of cancer after treatment. Two primary sources of resistance are the T790M Mutation and MET oncogenes (Jackman et al (2009)). However, as of 2010 there was no consensus of an accepted approach to combat resistance nor FDA approval of a specific combination. Preclinical results have been reported for AP26113 which targets the T790M mutation.

In the context of the immunoassays of the present invention the "EGF-receptor" may be present in its natural cellular environment and can be used together with the material associated with the receptor in its natural state as well as in isolated form with respect to its primary, secondary and tertiary structures. The EGF-receptor is well known to those skilled in the art. The receptor is preferably used in isolated form, i.e. essentially free of other proteins, lipids, carbohydrates or other substances naturally associated with the receptor. "Essentially free of" means that the receptor is at least 75%, preferably at least 85%, more preferably at least 95% and especially preferably at least 99% free of other proteins, lipids, carbohydrates or other substances naturally associated with the receptor.

In connection with the present invention, the naturally occurring receptor as well as all modifications, mutants or derivatives of the EGF-receptor can be used. Similarly, a EGF-receptor produced by means of recombinant techniques, which receptor includes amino acid modifications, such as inversions, deletions, insertions, additions etc. can be used according to the invention provided that this part of the essential function of the EGF-receptor is present, namely the capability of binding antibodies. The EGF-receptor being used may also comprise exceptional amino acids and/or modifications of such as alkylation, oxidation, thiol-modification, denaturation, oligomerization and the like. The receptor can also be synthesized by chemical means. According to the invention the EGF-receptor particularly can be a protein and/or peptide or a fusion protein, which in addition to other proteins, peptides or fragments thereof, includes the EGF-receptor as a whole or in part. Using conventional methods, peptides or polypeptides of the EGF-receptor which have functionally analogs, analogous properties can be determined by those skilled in the art. For example such polypeptides or peptides have 50-60%, 70% or 80%, preferably 90%, more preferably 95%, and most preferably 98% sequence homology to peptides identified as EGF-receptor, and said homology can be determined, e.g. by means of Smith-Waterman homology search algorithm, using the MPFRCH program (Oxford Molecular), for example.

The term "peptide" or "polypeptide" of an EGF-receptor used in the present invention, comprises also molecules differing from the original sequence by deletion(s), insertion(s), substitution(s) and/or other modifications well known in the prior art and/or comprising a fragment of the original amino acid molecule, the EGF-receptor still exhibiting the properties mentioned above. Such a peptide has preferably at least a length of 100 amino acid residues but may also be shorter, e.g. at least 12, 15, 20 or 25 amino acid residues in length. Also included are allele variants and modifications. Methods of producing the above changes in the amino acid sequence are well known to those skilled in the art and have been described in the standard textbooks of molecular biology, e.g. Sambrook et al., supra. Those skilled in the art will also be able to determine whether an EGF-receptor, thus, modified still has the properties mentioned above. The amino acid sequence of EGF-receptor is known. Database entries exist in several well known Databases. When refereeing to the amino acid sequence of EGF-receptor any amino acid sequence known is meant, particularly those disclosed in common databases. Until today database entries for EGF-receptor are known and include NCBI (NP_005219.2, GI:29725609; updated Jan. 18, 2014), CCDS (CCDS 5514.1), GeneID (Gene ID: 1956, updated on Jan. 19, 2014) Human Gene Nomenclature Commitee (HGNC:3236), and UniProt (P00533; uptaded on Dec. 11, 2013, Version 201). A preferred sequence of EGF-receptor is given as SEQ ID NO:1. The receptor may be glycosylated in vivo. In the present specification all of the above illustrated modifications of the EGFR-receptor will be referred to as "functionally analogous peptides or proteins" in brief In context with the present invention different terms may be used for antibodies directed against EGFR, e.g. "anti-EGFR", "EGFR antibody", "anti-EGFR antibody", "anti-EGF-receptor antibody" all relate to immunoglobulins directed and binding to EGFR. In case the antibodies are to be determined in the samples of the subjects or those in control subject, the antibody is meant to be an autoantibody, i.e. those produced by the subject itself. The antibodies to be detected or determined according to the present invention are directed against EGF-receptor. This means that the antibodies specifically bind EGF-receptor.

Specific binding of an antibody normally occurs via binding of a binding site of the antigen, i.e. EGF-receptor, the epitope. The antibodies of the present invention are those specifically binding to EGF-receptor. This binding may occur via recognition of sequence or structural epitopes. The skilled person is aware of methods of how to determine specific epitopes, e.g. fragments of the antigen EGF-receptor, which are recognized and bound by the antibodies to be determined. Fragments of EGF-receptor binding to the auto antibodies are called immunogenic fragments. Methods for determining fragments of an antigen binding the antibody are described in several publications (e.g. Gershoni, J M; Roitburd-Berman, A; Siman-Tov, D D; Tarnovitski Freund, N; Weiss, Y (2007). "Epitope mapping: The first step in developing epitope-based vaccines". BioDrugs 21 (3): 145-56; Westwood, M R; Hay, F C (2001). Epitope Mapping: a practical approach. Oxford, Oxfordshire: Oxford University Press. ISBN 0-19-963652-4; Flanagan et al. (2011), "Mapping Epitopes with H/D-Ex Mass Spec". Genetic Engineering and Biotechnology news; 31(1); Gaseitsiwe, S.; Valentini, D.; Mandavifar, S.; Reilly, M.; Ehrnst, A.; Maeurer, M. (2009) "Peptide Microarray-Based Identification of Mycobacterium tuberculosis Epitope Binding to HLA-DRB1*0101, DRB1*1501, and DRB1*0401". Clinical and Vaccine Immunology 17 (1): 168-75; Linnebacher, Michael; Lorenz, Peter; Koy, Cornelia; Jahnke, Annika; Born, Nadine; Steinbeck, Felix; Wollbold, Johannes; Latzkow, Tobias et al. (2012). "Clonality characterization of natural epitope-specific antibodies against the tumor-related antigen topoisomerase IIa by peptide chip and proteome analysis: A pilot study with colorectal carcinoma patient samples" Analytical and Bioanalytical Chemistry 403 (1): 227-38; Cragg, M. S. (2011). "CD20 antibodies: Doing the time warp". Blood 118 (2): 219-20; Banik, Soma S. R.; Doranz, Benjamin J. (2010). "Mapping Complex Antibody Epitopes". Genetic Engineering and Biotechnology News 3 (2): 25-8;

and Paes, Cheryl; Ingalls, Jada; Kampani, Karan; Sulli, Chidananda; Kakkar, Esha; Murray, Meredith; Kotelnikov, Valery; Greene, Tiffani A. et al. (2009). "Atomic-Level Mapping of Antibody Epitopes on a GPCR". Journal of the American Chemical Society 131 (20): 6952-4). In context with the present invention EGFR antibodies are understood as any immunoglobulin specifically recognizing/binding to EGFR, preferably the extracellular portion.

In the context of the present invention the anti-EGFR antibody may particularly be selected from the group of IgA-antibody, IgG-antibody and IgM-antibody, preferably an IgG antibody, e.g. IgG1, IgG2, IgG3 and IgG4.

Herein, the sample of the subject to be diagnosed in which the level of anti-EGFR antibodies is to be determined is preferably a bodily fluid such as whole blood or lymph or fractions of blood such as serum or plasma. Preferably in the context of the present invention the sample is plasma or serum.

Where appropriate, the sample may need to be homogenized, or extracted with a solvent prior to use in the present invention in order to obtain a liquid sample. A liquid sample hereby may be a solution or suspension. Liquid samples may be subjected to one or more pre-treatments prior to use in the present invention. Such pre-treatments include, but are not limited to dilution, filtration, centrifugation, concentration, sedimentation, precipitation, dialysis. Pre-treatments may also include the addition of chemical or biochemical substances to the solution, such as acids, bases, buffers, salts, solvents, reactive dyes, detergents, emulsifiers, chelators.

The control levels as disclosed herein refer to control levels of anti EGF-receptor antibodies. It will be readily understood by the skilled person that the control levels from subjects having the desired disease or response as defined in the methods and to which the determined levels are compared to, are not necessarily determined in parallel but may be represented by previously determined levels. Nevertheless, control levels may be determined in parallel. The skilled person with the disclosure of the present invention and his knowledge is able to determine such levels, as will be outlined herein below. Hence, the control levels of the present invention may be previously defined thresholds. Preferred thresholds are disclosed herein.

Figure 6:
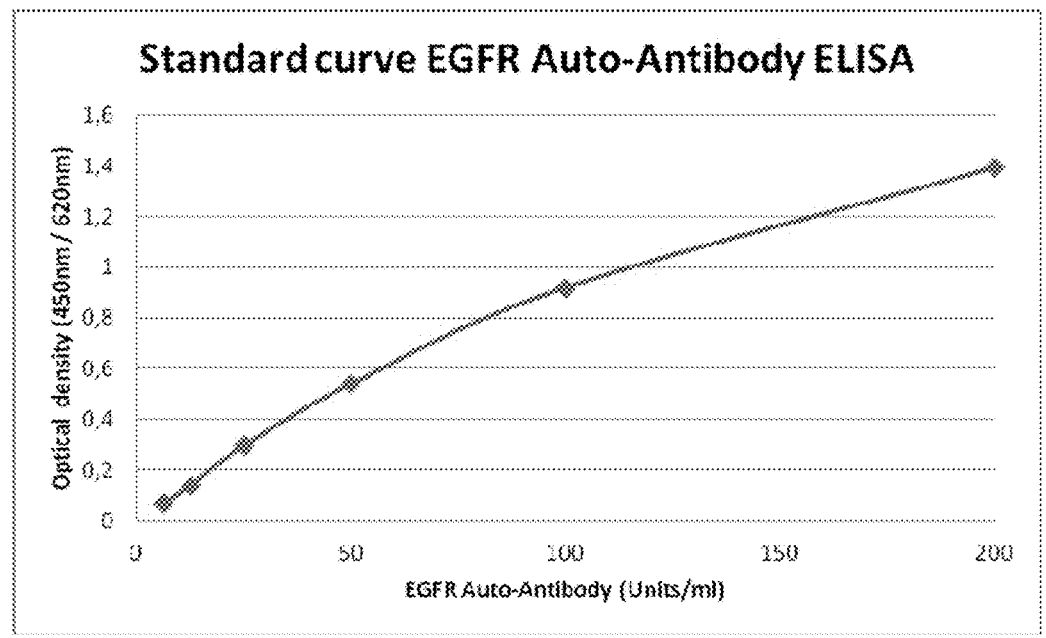
FIG. 6: Standard curve of the EGF-Receptor-Auto-Antibody ELISA

As outlined herein, the levels of EGFR antibodies in samples of the patient to be diagnosed and treated or to be treated are compared with the control groups as defined herein. However, in one embodiment the levels are compared to fixed values, i.e. thresholds under or over which a certain diagnosis, or prognosis of response is given. To this end, unit-standards may be applied. The present inventors set out such standard for the EGFR using serum samples from systemic sclerosis patients. Systemic sclerosis patients are known to have high levels of autoimmune antibodies in general. Hence, the inventors took a serum sample of a systemic sclerosis patient. However, it will be acknowledged by the skilled person that also other samples may be taken to set a different standard, e.g. samples of healthy subjects, samples of cancer patients. Nevertheless the principle of generating a standard (units) is the same in any case and are exemplified herein using serum samples of systemic sclerosis patients. In the context of the present invention "units/ml", unless specified otherwise, refers to the concentration of antibodies standardised as exemplified herein. Hence, in one embodiment of the present invention 100 units/ml refers to a dilution of 1:800 of a serum sample of systemic sclerosis patients. The serum sample may be derived from a single patient or of a cohort of a plurality of patients, e.g. a cohort of 200 patients suffering from systemic sclerosis. The present inventors found that the concentration of EGFR antibodies in samples of systemic sclerosis do not differ by more than about 10%, showing such standard being reproducible. In one preferred embodiment the standard for the concentrations of the autoimmune antibodies is generated in the following way: a serum sample of a systemic sclerosis patient (or a larger cohort) is diluted (a) 1:400 for standard point 200 Units/ml, (b) 1:800 for standard point 100 Units/ml, (c) 1:1600 for standard point 50 Units/ml, (d) 1:3200 for standard point 25 Units/ml, (e) 1:6400 for standard point 12.5 Units/ml and (0 1:12800 for standard point 6.25 Units/ml. These standards are then used for the immunoassay chosen, e.g. ELISA, and then correlated with the respective read-out value, e.g. for ELISA optical density at 450nm/optical density at 620 nm. A typical standard curve of an EGFR auto-antibody ELISA is shown in FIG. 6. Nevertheless, the skilled person will readily understand that it may also be possible to standardize the levels of EGFR-autoantibodies using different samples, e.g. samples of healthy subjects or cancer patients.

"Equal" level in the context of the present invention means that the levels differ by not more than±10%, preferably by not more than±5%, more preferably by not more than±2%. "Decreased" or "increased" level in the context of the present invention mean that the levels differ by more than 10%, preferably by more than 15%, preferably more than 20%.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood) for at least 15 minutes at 2000 to 3000 g.

"Serum" is the liquid fraction of whole blood that is collected after the blood is allowed to clot. When coagulated blood (clotted blood) is centrifuged serum can be obtained as supernatant. It does not contain fibrinogen, although some clotting factors remain.

In the method of the present invention, the anti-EGFR antibody is preferably detected in an immunoassay. Suitable immunoassays may be selected from the group of immunoprecipitation, enzyme immunoassay (EIA), enzyme-linked immunosorbenassys (ELISA), radioimmunoassay (RIA), fluorescent immunoassay, a chemiluminescent assay, an agglutination assay, nephelometric assay, turbidimetric assay, a Western Blot, a competitive immunoassay, a non-competitive immunoassay, a homogeneous immunoassay a heterogeneous immunoassay, a bioassay and a reporter assay such as a luciferase assay or Luminex® Assays. Preferably herein the immunoassay is an enzyme linked immunosorbent assay (ELISA).

The immunoassays can be homogenous or heterogeneous assays, competitive and non-competitive assays. In a particularly preferred embodiment, the assay is in the form of a sandwich assay, which is a non-competitive immunoassay, wherein the anti-EGFR antibody (i.e. the "analyte") to be detected and/or quantified is allowed to bind to an immobilized EGFR protein or immunogenic peptide fragment thereof and to a secondary antibody. The EGFR or fragment thereof (i.e. a peptide), may e.g., be bound to a solid phase, e.g. a bead, a surface of a well or other container, a chip or a strip, and the secondary antibody is an antibody which is labeled, e.g. with a dye, with a radioisotope, or a reactive or catalytically active moiety such as a peroxidase, e.g. horseradish peroxidase. The amount of labeled antibody bound to the analyte is then measured by an appropriate method. The general composition and procedures involved with "sandwich assays" are well-established and known to the skilled person (*The Immunoassay Handbook*, Ed. David Wild, Elsevier LTD, Oxford; 3rd ed. (May 2005), ISBN-13: 978-0080445267; Hultschig C et al., *Curr Opin Chem Biol*. 2006 February; 10(1): 4-10. PMID: 16376134, incorporated herein by reference). Sandwich immunoassays can for example be designed as one-step assays or as two-step assays.

The detectable label may for example be based on fluorescence or chemiluminescence. The labelling system comprises rare earth cryptates or rare earth chelates in combination with a fluorescence dye or chemiluminescence dye, in particular a dye of the cyanine type. In the context of the present invention, fluorescence based assays comprise the use of dyes, which may for instance be selected from the group comprising FAM (5-or 6-carboxyfluorescein), VIC, NED, Fluorescein, Fluoresceinisothiocyanate (FITC), IRD-700/800, Cyanine dyes, such as CY3, CYS, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in Kirk-Othmer, *Encyclopedia of chemical technology*, 4$^{th}$ ed., executive editor, J. I. Kroschwitz; editor, M Howe-Grant, John Wiley & Sons, 1993, vol. 15, p. 518-562, incorporated herein by reference, including citations on pages 551-562. Preferred chemiluminescent dyes are acridiniumesters.

The "sensitivity" of an assay relates to the proportion of actual positives which are correctly identified as such, i.e. the ability to identify positive results (true positives positive results/number of positives). Hence, the lower the concentrations of the analyte that can be detected with an assay, the more sensitive the immunoassay is. The "specificity" of an assay relates to the proportion of negatives which are correctly identified as such, i.e. the ability to identify negative results (true negatives/negative results). For an antibody the "specificity" is defined as the ability of an individual antigen binding site to react with only one antigenic epitope. The binding behaviour of an antibody can also be characterized in terms of its "affinity" and its "avidity". The "affinity" of an antibody is a measure for the strength of the reaction between a single antigenic epitope and a single antigen binding site. The "avidity" of an antibody is a measure for the overall strength of binding between an antigen with many epitopes and multivalent antibodies.

An "immunogenic peptide" or "antigenic peptide" as used herein is a portion of a EGFR protein that is recognized (i.e., specifically bound) by the anti-EGFR antibody. Such immunogenic peptides generally comprise at least 5 amino acid residues, more preferably at least 10, and still more preferably at least 20 amino acid residues of EGFR. However, they may also comprise at least 30, 40, 50, 60, 70, 80, 90, 100, 110, 120, 130, 140 or 150 amino acid residues. As outlined in Example 1, the antigen used in context with the examples was the membrane fraction of cells overexpressing EGFR. This means, that in a preferred embodiment of the present invention, the EGFR antibodies to be detected bind to the intra-or extra-cellular part of EGFR.

For the purposes of the immunoassays and diagnostic methods of the invention EGFR by expression in cells, preferably eukaryotic cells or in cell free, preferably eukaryotic cell free systems. Hence, in the assays and methods of the invention EGFR may be present in its natural cellular environment and can be used together with the material associated with the receptor in its natural state as well as in isolated form. Suitable expression systems include Chinese hamster ovary (CHO) cells overexpressing the human EGFR. Hence, cell extracts (particularly extracts from CHO cells overexpressing the human EGFR) can be used to detect anti-EGFR antibodies. Based on the weight of the whole receptor in the preparation (e.g. the "extract") to be used according to the invention, the isolated receptor should account for at least 0.5%, preferably at least 5% more preferably at least 25%, and in a particular preferred embodiment at least 50%. The receptor is preferably used in isolated form, i.e. essentially free of other proteins, lipids, carbohydrates or other substances naturally associated with the receptor. "Essentially free of" means that the receptor is at least 75%, preferably at least 85%, more preferably at least 95% and especially preferably at least 99% free of other proteins, lipids, carbohydrates or other substances naturally associated with the receptor.

In particular, the method of the present invention comprises the steps of (a) contacting the sample with EGFR or an antigenic peptide fragment under conditions allowing for the formation of a complex between anti-EGFR antibodies with EGFR or the antigenic peptide fragment thereof, (b) detecting the complex.

Hence, the invention relates to an immunoassay method for detecting a anti-EGFR antibody in a sample from a subject, comprising the steps of (a) contacting the sample suspected of comprising an anti-EGFR antibody with EGFR or an antigenic peptide fragment thereof under conditions allowing for the formation of a complex between the anti-EGFR antibody with EGFR or the antigenic peptide fragment thereof, (b) detecting the complex.

The EGFR or the antigenic peptide fragment thereof may preferably be immobilized on a surface. The complex may for example be detected using a secondary antibody against the Fc portion of the anti-EGFR antibody. When the anti-EGFR antibody is an IgG-antibody, the secondary antibody may be an anti-IgG antibody. In a particular embodiment, the subject is a human and (i) the anti-EGFR antibody is a IgG1-antibody and the secondary antibody is an anti-human-IgG1 antibody; or (ii) the anti-EGFR antibody is a IgG2-antibody and the secondary antibody is an anti-human-IgG2 antibody; or (iii) the anti-EGFR antibody is a IgG3-antibody and the secondary antibody is an anti-human-IgG3 antibody; or (iv) the anti-EGFR antibody is a IgG4-antibody and the secondary antibody is an anti-human-IgG4 antibody. The secondary antibody may for example be labeled with a detectable marker, e.g. a peroxidase.

Furthermore, in the methods of the present invention further parameters of the subject may considered as well. Such parameters in a multivariate model may include gender, age, histological evaluation, Figo or histopathological staging, grading of the tumor and other markers. Dependent variables for determining survival may also be time till death, time till first relapse, time till death or first relapse (shorter interval if both events occurred). A Cox-Proportional-Hazard regression predicts the dependent variable based on one or more independent variables. These predictors can either be measures (as e.g. level of a biomarker) or categorical data (as e.g. response to a previous treatment). The skilled person is aware of the fact that diagnostic markers only give a certain degree of sensitivity and specificity, as also outlined herein. He knows that different further parameters might be considered in order to increase both. For example, when detecting levels of a marker indicative for an EGF or EGFR associated cancer, inter alia ovarian cancer, the skilled person would not diagnose ovarian cancer in a male human subject. Nevertheless, the present invention provides a new and superior marker for diagnosis, prognosis of cancer, particularly for ovarian cancer. In the context of the methods of the invention and particularly the immunoassays of the invention, the presence of one or more further diagnostic markers for ovarian cancer is detected in the sample. For example, in a diagnostic method of the present invention levels of CA125, Human Epidymis Protein 4 (HE4) and/or Mesothelin are detected in addition.

The invention also relates to the use of EGFR or an antigenic peptide fragment thereof for the diagnosis of cancer, preferably for the diagnosis of an EGF or EGFR associated cancer, more preferably for the diagnosis of a cancer selected from the group consisting of ovarian cancer, lung cancer, renal cancer, colon cancer, and colorectal cancer, preferably ovarian cancer.

In the context of the present invention, the levels of the anti-EGFR antibodies a may be analyzed in a number of fashions well known to a person skilled in the art. For example, each assay result obtained may be compared to a "normal" value, or a value indicating a particular disease or outcome. A particular diagnosis/prognosis may depend upon the comparison of each assay result to such a value, which may be referred to as a diagnostic or prognostic "threshold". In certain embodiments, assays for one or more diagnostic or prognostic indicators are correlated to a condition or disease by merely the presence or absence of the indicator(s) in the assay. For example, an assay can be designed so that a positive signal only occurs above a particular threshold concentration of interest, and below which concentration the assay provides no signal above background.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy individuals not having ovarian cancer) and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, below which the test is considered to be abnormal and above which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art. See, e.g., Hanley et al. 1982. *Radiology* 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to+/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group.

The skilled artisan will understand that associating a diagnostic or prognostic indicator, with a diagnosis or with a prognostic risk of a future clinical outcome is a statistical analysis. For example, a marker level of lower than X may signal that a patient is more likely to suffer from an adverse outcome than patients with a level more than or equal to X, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, *Statistics for Research*, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

Suitable threshold levels for the stratification of subjects into different groups (categories) have to be determined for each particular combination of EGFR-antibodies, disease and/or medication. This can e.g. be done by grouping a reference population of patients according to their level of EGFR-antibodies into certain quantiles, e.g. quartiles, quintiles or even according to suitable percentiles. For each of the quantiles or groups above and below certain percentiles, hazard ratios can be calculated comparing the risk for an adverse outcome, i.e. an "cancer" or a "non response", e.g. in terms of survival rate/mortality, between those patients who have received a certain medication and those who did not, or in terms of presence and absence of cancer in patients. In such a scenario, a hazard ratio (HR) above 1 indicates a higher risk for an adverse outcome for the patients who have received a treatment than for patients who did not. A HR below 1 indicates beneficial effects of a certain treatment in the group of patients. A HR around 1 (e.g.+/− 0.1) indicates no elevated risk but also no benefit from medication for the particular group of patients. By comparison of the HR between certain quantiles of patients with each other and with the HR of the overall population of patients, it is possible to identify those quantiles of patients who have an elevated risk and those who benefit from medication and thereby stratify subjects according to the present invention.

In some cases presence of cancer, relapse and/or mortality upon treatment with an angiogenesis inhibitor will affect patients with high levels (e.g. in the fifth quintile) of EGFR-antibodies, while in other cases only patients with low levels of EGFR-antibodies will be affected (e.g. in the first quintile). However, with the above explanations, a skilled person is able to identify those groups of patients having cancer, those groups that do respond to a medication and those groups that do not respond to the medication. Exemplarily, some combinations of hormones and medications are listed for several diseases in the appended examples. In another embodiment of the invention, the diagnosis, risk for relapse of cancer and/or mortality and/or outcome for a patient are determined by relating the patient's individual level of marker peptide to certain percentiles (e.g. $97.5^{th}$ percentile) of a healthy population.

Kaplan-Meier estimators may be used for the assessment or prediction of the outcome or risk (e.g. diagnosis, relapse, progression or morbidity) of a patient.

The invention also pertains to a research and/or diagnostic kit for the diagnosis of cancer, e.g. ovarian cancer, or for the prediction of risk stratification for relapse of cancer and/or mortality in a patient, wherein the kit comprises EGFR or an antigenic peptide fragment thereof. The kit may further comprise an antibody directed to the Fc portion of the anti-EGFRantibody to be detected, i.e. an anti-human IgG antibody.

Such kits can comprise a carrier, package or container that is compartmentalized to receive one or more containers such as vials, tubes, and the like, each of the container(s) comprising one of the separate elements to be used in the method. The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for either in vivo or in vitro use, such as those described herein. Directions and or other information can also be included on an insert which is included with the kit.

The term "drug" in connection with the present invention is to be understood as any substance, pharmaceutical composition or the like which are intended for the treatment of cancer, preferably an EGF or EGFR associated cancer as outlined herein, particularly preferred ovarian cancer. Different drugs are known. Preferred drugs are inhibitors of EGFR activity, e.g. those blocking EGF binding to EGFR or agents inhibiting the kinase activity of the EGF-receptor. The inventors found response of patients suffering from cancer to a drug inhibiting EGFR, e.g. panitumumab, may be predicted by determining the levels of anti-EGFR antibodies in samples from a patient to be treated. Panitumumab (INN), formerly ABX-EGF, is a fully human monoclonal antibody specific to the epidermal growth factor receptor. Panitumumab is manufactured by Amgen and marketed as Vectibix. It was originally developed by Abgenix Inc. Panitumumab works by binding to the extracellular domain of the EGFR preventing its activation. This results in halting of the cascade of intracellular signals dependent on this receptor (Plunkett, Jack W. (Sep. 30, 2005). Plunkett's Biotech & Genetics Industry Almanac 2006. Plunkett Research, Ltd. ISBN 1-59392-033-4). In a preferred embodiment the drug used for the treatment of cancer are drugs directed against EGFR, e.g. antibodies binding EGFR, preferably at the extracellular part, and inhibitors of EGFR acitivity. Such inhibitors are known and include panitumumab, cetuximab, zalutumumab, nimotuzumab, matuzumab, gefitinib, erlotinib, lapatinib, vandetanib, and trastuzumab, which are preferred drugs in connection with the present invention, particularly preferred is panitumumab.

The drug is preferably a drug as defined herein. In a preferred embodiment the drug used for the treatment of cancer is an inhibitor of EGFR activity. A representative member has been tested and its predictive and prognostic value has been confirmed in the examples provided herewith. Hence, the invention also relates to a method for determining whether a subject being treated or to be treated for cancer with an inhibitor of EGFR activity will respond to said treatment comprising the steps of (i) determining the level of antibodies against EGFR in a sample from said subject being treated or to be treated; and (ii) comparing the determined level in the sample to either one or both of a first and second EGFR antibody control level, a) wherein the first EGFR antibody control level is derived from subjects responding to said treatment, and b) wherein the second EGFR antibody control level is derived from subjects not responding to said treatment, wherein a decreased level in the sample from the subject being treated or to be treated as compared to the first EGFR antibody control level and/or an equal level as compared to the second EGFR antibody control level is indicative for a non-response of said subject to said treatment, and wherein an increased level in the sample from the subject being treated or to be treated as compared to the second EGFR antibody control level and/or an equal level as compared to the first EGFR antibody control level is indicative for a response of said subject to said treatment. In one embodiment of the method for determining whether a subject being treated or to be treated for cancer with an inhibitor of EGFR activity will respond to said treatment, a level of antibodies against EGFR in the sample from the subject to be treated of less than 0.9 fold as compared to the first EGFR antibody control level is indicative for a non-response of said subject to said treatment with an inhibitor of EGFR activity, preferably a level of antibodies against EGFR in the sample from the subject to be treated of less than 0.6 fold as compared to the first EGFR antibody control level is indicative for a non-response of said subject to said treatment with an inhibitor of EGFR activity, further preferred a level of antibodies against EGFR in the sample from the subject to be treated of less than 0.5 fold as compared to the first anti-EGFR control level is indicative for a non-response of said subject to said treatment with an inhibitor of EGFR activity; yet further preferred a level of antibodies against EGFR in the sample from the subject to be treated of less than 0.25 fold as compared to the first anti-EGFR control level is indicative for a non-response of said subject to said treatment with an inhibitor of EGFR activity. Likewise, ratios may be determined for the response. In such embodiment a level of antibodies against EGFR in the sample from the subject to be treated of more than 1.1 fold as compared to the second EGFR antibody control level is indicative for a response of said subject to said treatment with an inhibitor of EGFR activity, preferably a level of antibodies against EGFR in the sample from the subject to be treated of more than 1.5 fold as compared to the second EGFR antibody control level is indicative for a response of said subject to said treatment with an inhibitor of EGFR activity, further preferred a level of antibodies against EGFR in the sample from the subject to be treated of more than 2 fold as compared to the second anti-EGFR control level is indicative for a response of said subject to said treatment with an inhibitor of EGFR activity; yet further preferred a level of antibodies against EGFR in the sample from the subject to be treated of more than 4.0 or even 4.5 fold as compared to the second anti-EGFR control level is indicative for a response of said subject to said treatment with an inhibitor of EGFR activity. Preferred inhibitors of EGFR activity are disclosed herein. One particular preferred inhibitor of EGFR activity is panitumumab. Preferably, the subject is to be treated.

Also encompassed by the invention is a method of treating ovarian cancer in a subject, comprising determining the level of antibodies against EGFR in a sample from the subject, wherein when the level of anti-EGFR antibodies in a sample from the subject is above10.0 units/ml, a drug as defined herein is administered to the subject; preferably above 20 units/ml, more preferred above 30 units/ml, further preferred above 40 units/ml. In a particular embodiment the patient is treated at levels of EGFR antibodies above 34 units/ml.

The invention, thus, also relates a drug for use in the treatment of cancer in a subject, wherein the drug is administered to the subject when the level anti-EGFR antibodies in a sample from the subject is above10.0 units/ml, preferably above 20 units/ml, more preferred above 30 units/ml, further preferred above 40 units/ml. In a particular embodiment the the drug is administered when the level of anti-EGFR antibodies above 34 units/ml. . In a preferred embodiment the drug is for use in the treatment of an EGFR associated cancer, preferably selected from the group consisting of ovarian cancer, colorectal cancer, colon lung cancer, breast cancer, glioblastoma, and kidney (renal) renal . The drug is preferably selected from the group consisting of panitumumab, cetuximab, zalutumumab, nimotuzumab, matuzumab, gefitinib, erlotinib, lapatinib, vandetanib, and trastuzumab. In a further preferred embodiment the drug is EGFR inhibitor, preferably panitumumab. The invention, thus, also relates to panitumumab for use in the treatment of ovarian cancer in a subject, wherein panitumumab is administered to the subject when the level anti-EGFR antibodies in a sample from the subject is above10.0 units/ml, preferably above 20 units/ml, more preferred above 30 units/ml, further preferred above 40 units/ml. In a particular embodiment the the drug is administered when the level of anti-EGFR antibodies above 34 units/ml.

The invention furthermore relates to a kit for diagnosing cancer as outlined above, or predicting the response of a cancer patient to the treatment for cancer, said kit comprising EGFR or an antigenic peptide thereof, and means to detect antibodies binding to said EGFR or peptide thereof. Preferably the kit is designed for a method of the present invention. It will be understood that the embodiments disclosed herein above for EGFR or an antigenic peptide thereof as set out herein above also apply to the kit. The kit is designed to detect autoimmune antibodies in samples of subject and hence comprises means to detect such antibodies, particularly antibodies binding to said EGFR or peptide thereof. Such means are outlined herein above, e.g. for immunoassays. The embodiments set out for the immunoassays apply also to the kit of the invention. The kits of the present invention are meant for the detection of autoimmune antibodies. Hence, in one embodiment they comprise means for the preparation of blood, e.g. for gaining serum thereof. Furthermore, the kit may comprise control composition and/or standards. The control composition preferably comprises a EGFR antibodies as positive control. Furthermore, the kit may comprise one or a plurality of standard compositions. A standard composition comprises EGFR antibodies at a defined concentration. As outlined herein, determination of concentration of autoimmune-antibodies may be performed using standard curves. These curves set out which concentration of antibodies in a sample or solution corresponds to what read-out value of the assay used, e.g. optical density or proportion of optical density at different wavelengths (e.g. 450 nm/620 nm). To this end the kits of the present invention may comprise one or more standard compositions having a defined concentration of EGFR antibodies, preferably of the kind to be detected in the method. A standard composition of the kits according to the present invention comprise EGFR antibodies at concentrations selected from the group consisting of 200 units/ml, 100 units/ml, 50 units/ml, 25 units/ml, 12.5 units/ml, and 6.25 units/ml. In one embodiment the kit comprises six standard compositions with the recited concentration. In another embodiment the kit comprises one standard composition with the highest concentration of the standard curve, e.g. 200 units/ml or 100 units/ml. The other concentrations may be produced at the side of the end user by further dilutions, e.g. in PBS. A dilution buffer may therefore also be comprised in the kits according to the invention.

It will be readily understood that the embodiments outlined above shall apply to the invention as a whole and not be limited to a specific method, unless stated otherwise. It will for example be understood the embodiments for the type of cancer shall be applied to every method, kit or the like disclosed herein. The invention is further illustrated by the following non-limiting examples and figures.

Sequences

```
SEQ ID NO: 1:
Amino acid sequence of the human EGF-receptor [SEQ ID NO: 1]:
   1   MRPSGTAGAA LLALLAALCP ASRALEEKKV CQGTSNKLTQ LGTFEDHFLS

51   LQRMENNCEV VLGNLEITYV QRNYDLSFLK TIQEVAGYVL IALNTVERIP
```

```
                    -continued
101   LENLQIIRGN MYYENSYALA VLSNYDANKT GLKELPMRNL QEILHGAVRF

151   SNNPALCNVE SIQWRDIVSS DFLSNMSMDF QNHLGSCQKC DPSCPNGSCW

201   GAGEENCQKL TKIICAQQCS GRCRCKSPSD CCHNQCAACC TGPRESDCLV

251   CRKFRDEATC KDTCPPLMLY NPTTYQMDVN PEGKYSFGAT CVKKCPRNYV

301   VTDHGSCVRA CGADSYEMEE DGVRKCKKCE CPCRKVCNCT GIGEFKDSLS

351   INATNIKHFK NCTSISGDLH ILPVAFRGDS FTHTPPLDPQ ELDILKTVKE

401   ITGELLIQAW PENRTDLHAF ENLEIIRGRT KQHGQFSLAV VSLNITSLGL

451   RSLKEISDGD VIISCNKNLC YANTINWKKL FCTSGQKTKI ISNRGENSCK

501   ATGQVCHALC SPECCWOPEP RDCVSCRNVS RGRECVDKCN LLEGEPREFV

551   ENSECIQCHP ECLPQAMNIT CTGRGPDNCI QCARYIDGPE CVKTCPAGVM

601   GENNTLVWKY ADAGEVCHLC HPNCTYGCTG PGLECCPTNO PKIPSIATGM

651   VGALLLLLVV ALGIGLFMRR RHIVRKRTLR RLLQERELVE PLTPSGEAPN

701   QALLRILKET EFKKIKVLGS OAFGTVYKCL WIPEGEKVKI PVAIKELREA

751   TSPKANKEIL DEAYVMASVD NPHVCRLLGI CLTSTVQLIT QLMPFGCLLD

801   YVREHKDNIG SQYLLNWCVQ IAKGMNYLED RRLVHRDLAA RNVLVKTPQH

851   VKITDFCLAK LLGAEEKEYH AEGCKVPIKW MALESILHRI YTHQSDVWSY

901   GVTVWELMTF GSKPYDOIPA SEISSILEKG ERLPQPPICT IDVYMIMVKC

951   WMIDADSRPK FRELIIEFSK MARDPQRYLV IQGDERMHLP SPTDSNFYRA

1001  LMDEEDMDDV VDADEYLIPQ QGTESSPSTS RTPLLSSLSA TSNNSTVACI

1051  DRNGLQSCPI KEDSFLQRYS SDPTGALTED SIDDTFLPVP EYINQSVPKR

1101  PAGSVQNPVY HNQPLNPAPS RDPHYQDPHS TAVGNPEYLN TVQPTCVNST

1151  FDSPAHWAQK CSHQISLDNP DYQQDFFPKE AKPNGIFKGS TAENAEYLRV

1201  APQSSEFIGA
```

EXAMPLES

Example 1

We measured the anti-EGFR autoantibody in serum samples using a sandwich ELISA kit (CellTrend GmbH Luckenwalde, Germany). The microtiter 96-well polystyrene plates were coated with membrane extracts of a cancer cell line "A431" human EGFR of SEQ ID NO:1. To maintain the conformational epitopes of the receptor, 1 mM calcium chloride was added to every buffer. Duplicate samples of a 1:100 serum dilution were incubated at 4° C. for 2 hours. After washing steps, plates were incubated for 60 minutes with a 1:20.000 dilution of horseradish-peroxidase—labeled goat anti-human IgG (Jackson, USA) used for detection. In order to obtain a standard curve, plates were incubated with test sera from an anti-EGFR autoantibody positive index patient. The ELISA was validated according to the FDA's "Guidance for industry: Bioanalytical method validation".

To set a standard for the concentrations of the autoimmuno antibodies, a standard curve was generated In detail, a serum sample of a systemic sclerosis patient was diluted (a) 1:400 for standard point 200 Units/ml, (b) 1:800 for standard point 100 Units/ml, (c) 1:1600 for standard point 50 Units/ml, (d) 1:3200 for standard point 25 Units/ml, (e) 1:6400 for standard point 12.5 Units/ml and (0 1:12800 for standard point 6.25 Units/ml. Then the optical density was determined using the kit and method as set out above. Each standard point was performed in duplicates. A typical standard curve of an EGFR auto-antibody ELISA is shown in FIG. 6.

Example 2:

Anti-EGFR antibody levels in serum samples from 131 healthy donors ("control") and 201 patients with ovarian cancer ("case") were measured using the kit and method of Example 1. The levels were determined in units/mL. FIG. 1 shows the mean values of the natural logarithm of the EGFR antibody level for case and control subjects. Patient suffering from ovarian cancer had significantly lower levels (p≤0.0001) of anti-EGFR antibodies as compared to healthy controls.

Example 3

Figure 2:
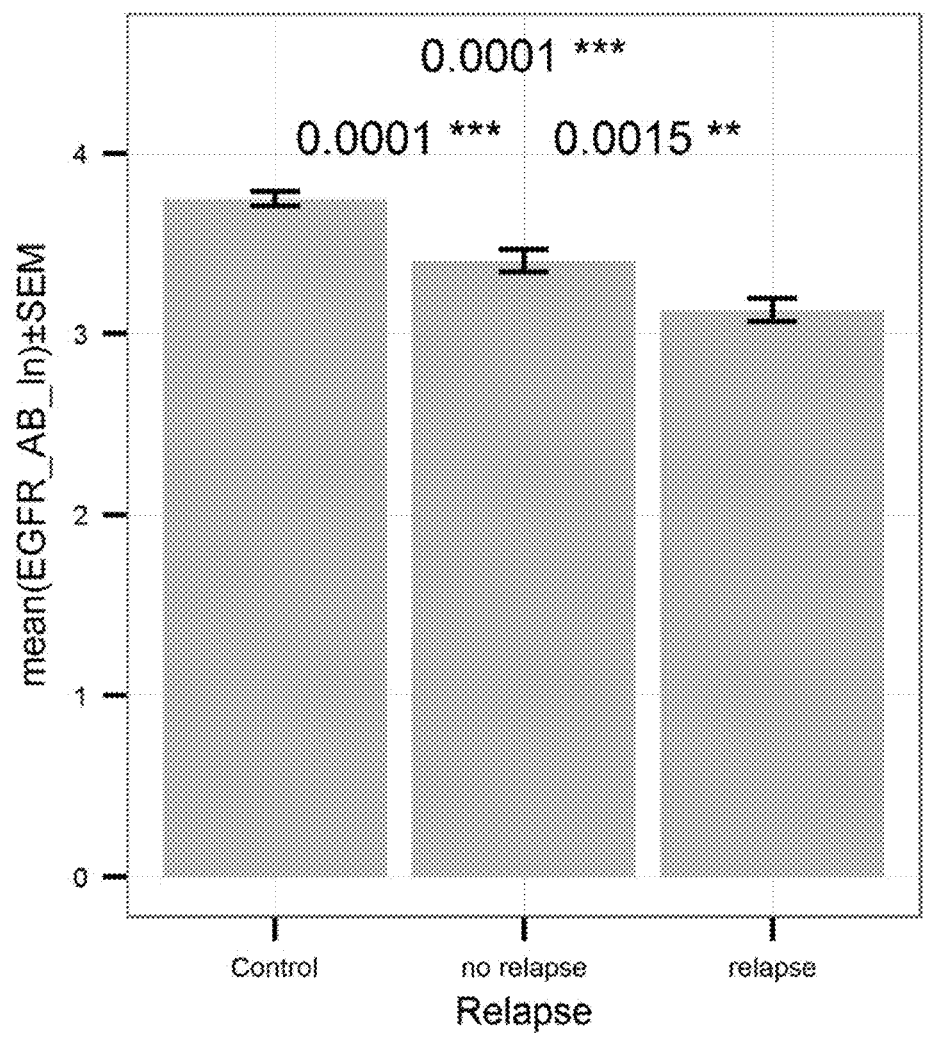
FIG. 2: Comparison of the mean level of anti-EGFR antibodies (ln of units/ml) in serum samples of ovarian cancer patients showing no relapse (ln of mean=3.407; n=77) to the mean level of anti-EGFR antibodies in serum samples of ovarian cancer patients showing relapse of ovarian cancer after surgical removal of the tumor and subsequent chemotherapy with cisplatin or carboplatinum (ln of mean=3.133; n=123). The column on the left indicates the levels of anti-EGFR antibodies in healthy subjects (for details see FIG. 1). Numbers above the columns indicate p-values (0.0001 between "control" and "relapse" as well as between "control" and "no relapse"; 0.0015 between "no relapse" and "relapse"). Bars indicated standard error of mean.

Levels of the EGFR-antibody were compared in patients showing relapse of ovarian cancer after therapy and patients showing no relapse. Treatment was surgical removal of the tumor and subsequent chemotherapy with cis platinum or carboplatinum conducted and monitored by physicians. Samples of patients were taken before treatment. Patients were categorized as "relapse" or "no relapse" according to the reoccurrence of cancer after a period of 24 months. Levels of EGFR-antibody were determined as outlined in Example 1. EGFR-AA levels are significantly higher in patients who had no relapse, compared to patients who had a relapse (p=0.0044). The determined levels were also compared to the control group of healthy subjects. These results are shown in FIG. 2.

Example 4

Figure 3:
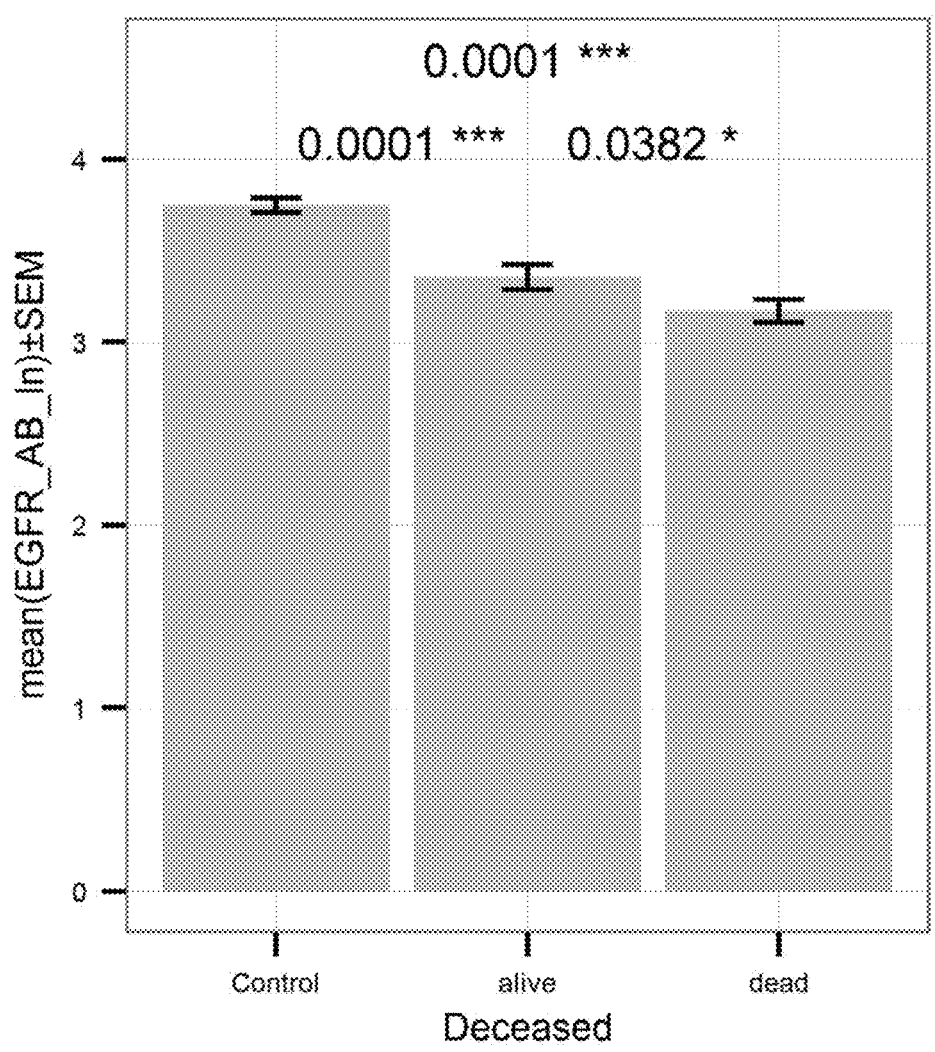
FIG. 3: Comparison of the mean level of anti-EGFR antibodies (ln of units/ml) in serum samples of ovarian cancer patients who survived after surgical removal of the tumor and subsequent chemotherapy with cisplatin or carboplatinum ("alive"; mean=3.355; n=71) to the mean level of anti-EGFR antibodies in serum samples of ovarian cancer patients who died after surgical removal of the tumor and subsequent chemotherapy with cisplatin or carboplatin ("dead"; mean=3.172 units/ml; n=128). The left column gives the healthy control group. P-values are indicated above (0.0001 between "control" and "alive" as well as between "control" and "dead", and 0.0382 between "alive" and "dead"). Bars indicate standard error of mean.

Serum samples of ovarian cancer patients were taken before surgical removal of the tumor and subsequent chemotherapy with cis platinum or carboplatin. The treatment was conducted and monitored by physicians. The patients were categorized into survivors ("survival") and patients who died after treatment ("death"). The levels of anti-EGFR antibodies were determined as outlined in Example 1. The results are shown in FIG. 3. Levels of anti-EGFR antibodies were lower in patients of the "death" group (mean ln of unit/ml=3.172) compared to the "survival" group (mean ln of unit/ml=3.355), the different was significant (p=0.038).

Example 5

Figure 4:
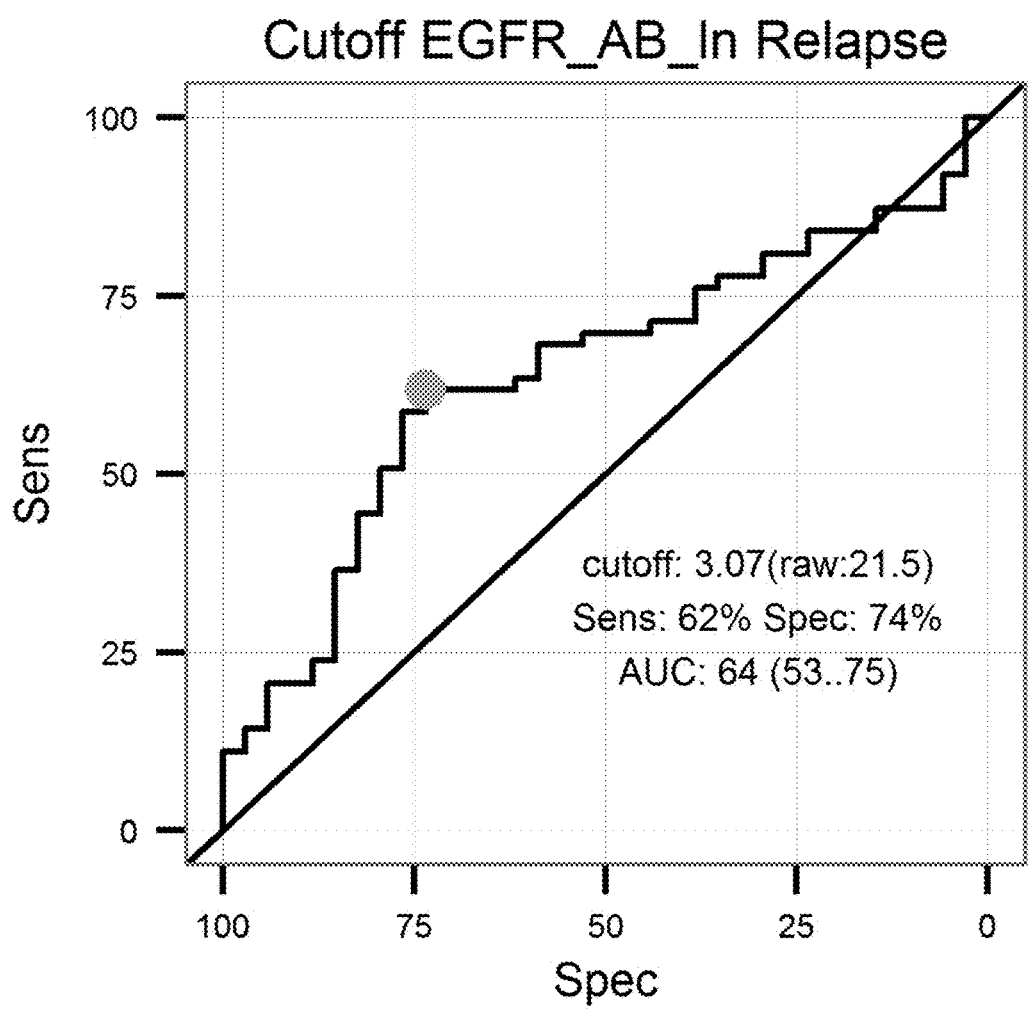
FIG. 4: A: on top sensitivity of the prediction of relapse of ovarian cancer after surgical removal of the tumor and subsequent chemotherapy with cisplatin or carboplatin is plotted against the specificity. Cutoff value (ln of units/ml=3.07) and AUC is given in the graph. Below Kaplan-Meier estimators with the proportion of patients not showing relapse after surgical removal of the tumor and subsequent chemotherapy with cisplatin or carboplatin is shown over the time for patients having antibody levels below the ROC-cutoff value (dotted line) and above the ROC-cutoff value (solid line). B: on top sensitivity of the prediction of survival after surgical removal of the tumor and subsequent chemotherapy with cisplatin or carboplatin is plotted against the specificity. Cutoff value (ln of units=3.13) and AUC is given in the graph. Below Kaplan-Meier estimators with the proportion of patients surviving after surgical removal of the tumor and subsequent chemotherapy with cisplatin or carboplatin is shown over the time for patients having antibody levels below the ROC-cutoff value (dotted line) and above the ROC-cutoff value (solid line). C: on the left sensitivity of the prediction of a combined endpoint (death or relapse of cancer) of ovarian cancer patients after surgical removal of the tumor and subsequent chemotherapy with cisplatin or carboplatinis plotted against the specificity. Cutoff value (ln of units/ml=3.13) and AUC is given in the graph. Below Kaplan-Meier estimators with the proportion of patients surviving or not showing relapse of cancer aftersurgical removal of the tumor and subsequent chemotherapy with cisplatin or carboplatin is shown over the time for patients having antibody levels below the ROC-cutoff value (dotted line) and above the ROC-cutoff value (solid line).
Figure 4:
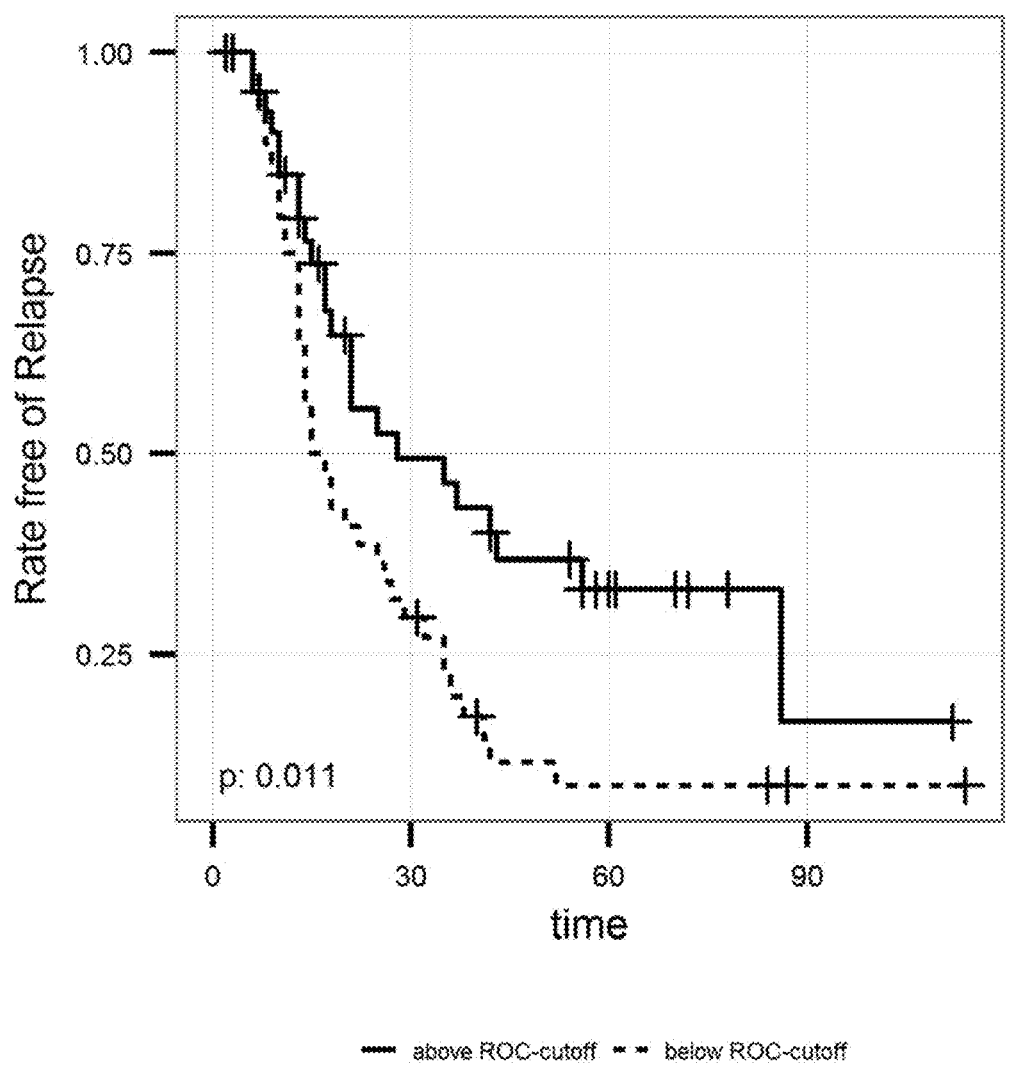
Figure 4:
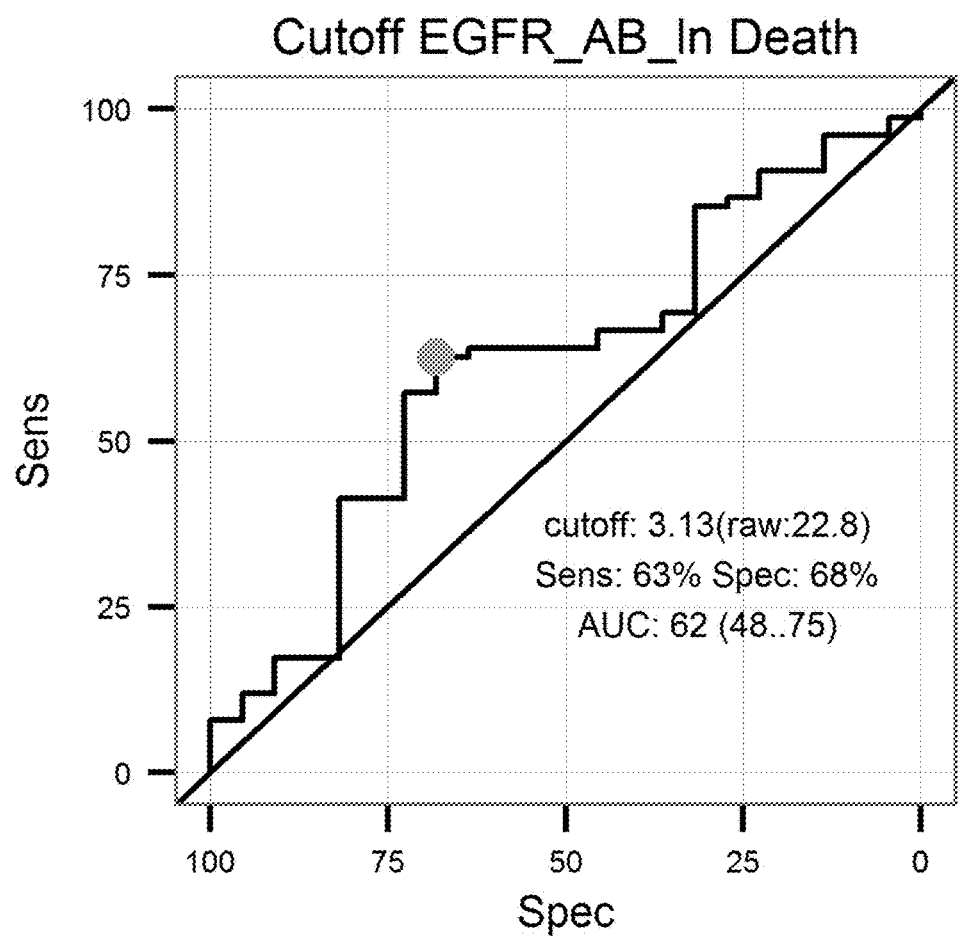
Figure 4:
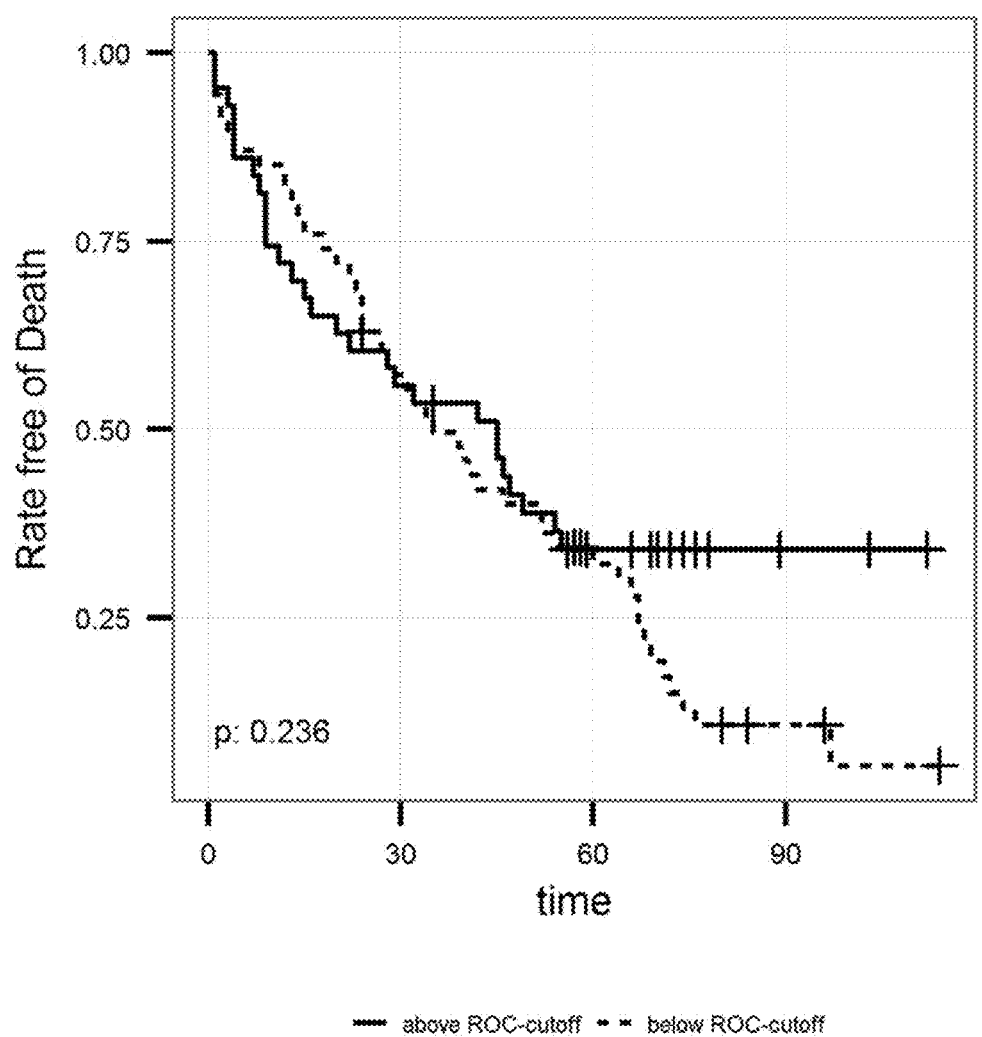
Figure 4:
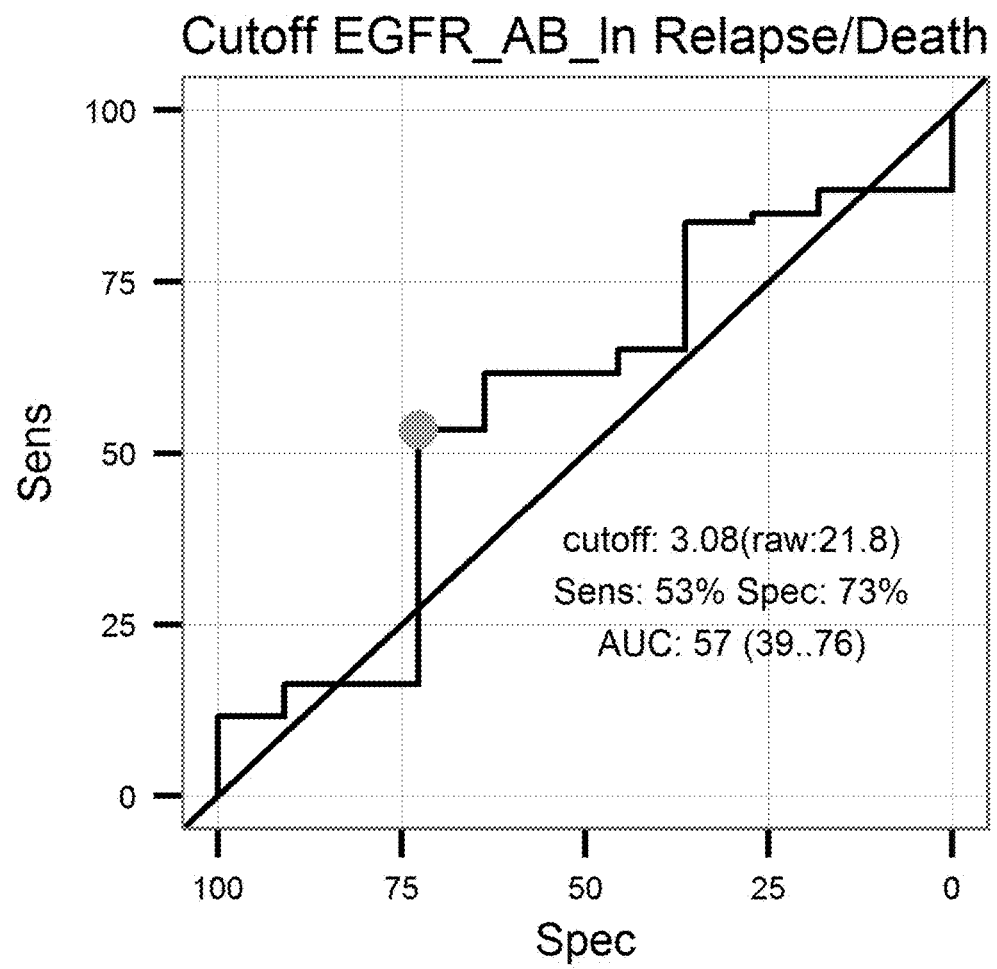
Figure 4:
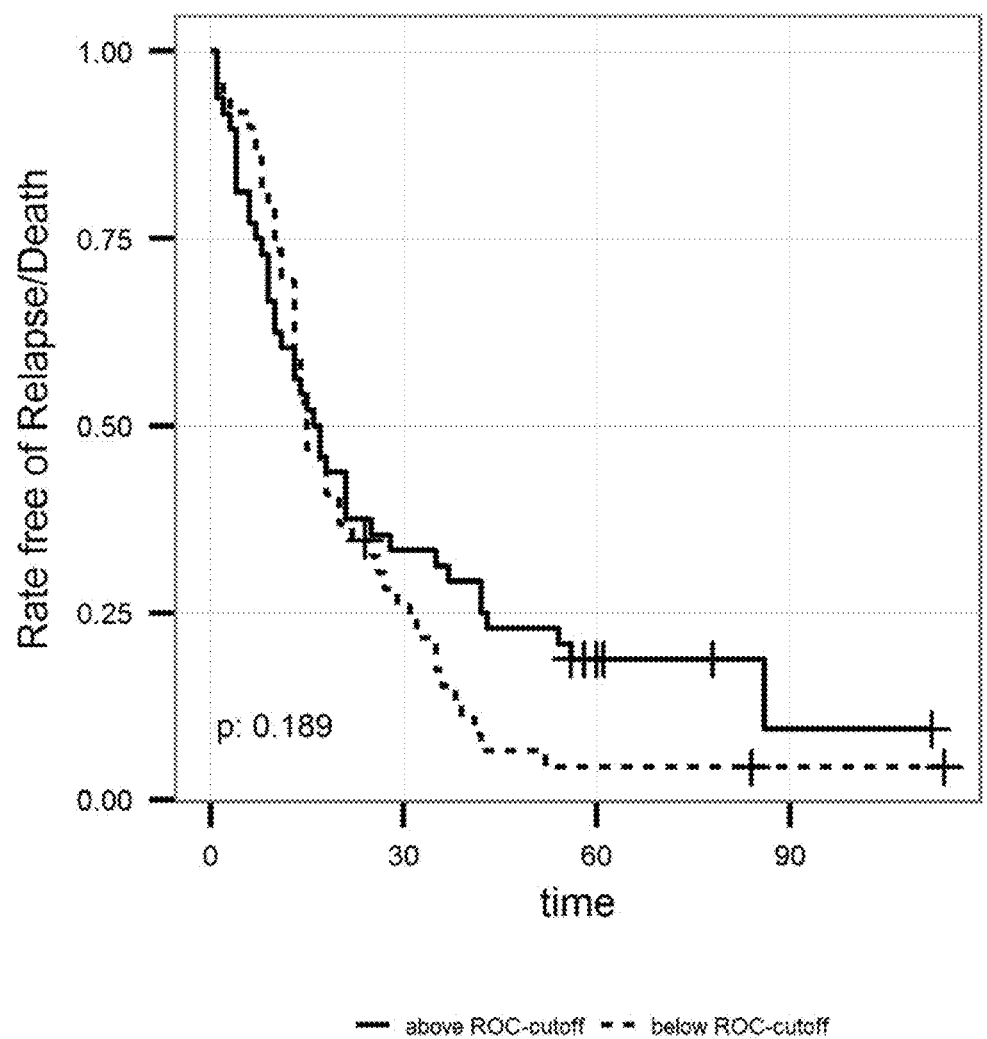

The sensitivity and specificity for levels of anti-EGFR antibodies as predictor of relapse and/or mortality was calculated using ROC-anlayis. The results for the prediction of relapse are given in FIG. 4A, for the prediction of mortality in FIG. 4B, and for the combined endpoint prediction (relapse or death) in FIG. 4C. The results show that the levels of anti-EGFR antibodies are a good predictor for relapse or mortality after treatment of cancer patients as endpoint prediction. The specificity and sensitivity of the prediction could be further enhanced when including further factors in a multivariate model. These factors were age, Figo and histology staging. The p-value for mortality or the combined end-point (mortality or relapse) was p<0.001 and p<0.011, respectively in the Cox-proportional hazard. For relapse as the single endpoint we observed a significant value. The p-value was 0.01.

Example 6

Figure 5:
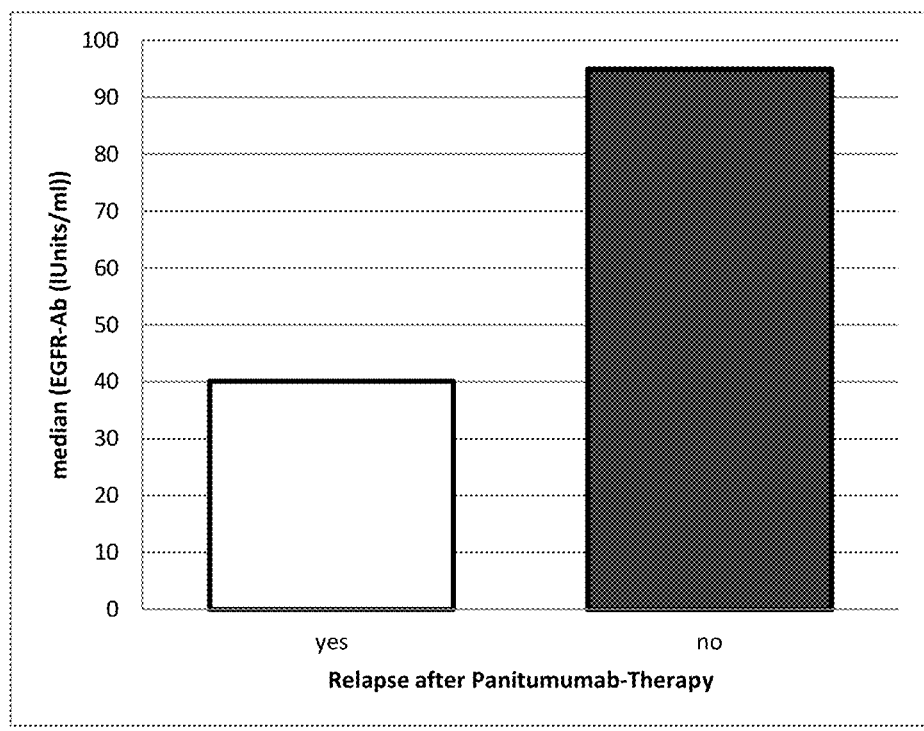
FIG. 5: Prediction of survival after treatment of ovarian cancer with panitumumab (Vectibix). Samples were taken before onset of treatment. Levels of antibodies directed against EGFR were measured . The patients were categorized in relapse after panitumumab treatment or no relapse after panitumumab treatment and showed mean values for EGFR antibody levels of 95.0 units/ml (relapse free) or 40.1 units/ml (relapse), respectively. (The mean of patients with a relapse was elevated because of one patient showing relapse and having high EGFR antibody levels. Not counting this patient the mean of patients showing relapse is about 20 units/ml).

Panitumumab is a humanized monoclonal antibody that is an EGFR inhibitor. Levels of autoantibodies directed against EGFR were measured in patients suffering from ovarian cancer as outlined in Example 1 in samples taken before Panitumumab treatment. The patients were categorized into relapse "yes" and "no", indicating whether they survived after the treatment or not. Results are given in FIG. 5. Patients of the "yes" group showed a significant lower level of anti EGFR antibodies in samples as compared to patients of the "no" group. This clearly shows that levels of anti EGFR antibodies are a good predictor for the response after treatment of cancer with an EGFR inhibitor.

SUMMARY

The results of the present Examples show that anti-EGFR antibody levels are significant lower in patients with ovarian cancer compared to healthy controls. Furthermore, the levels are significantly higher in patients in which show no relapse after treatment with chemotherapeutic agents or an inhibitor of EGFR activity. Levels of anti-EGFR antibody in patients suffering from an ovarian cancer with serous histopathology are higher compared to samples from patients suffering from ovarian cancer with non-serous histopathology. Levels of anti-EGFR antibodies in samples are a well suited predictor for the response to the treatment with an angiogenesis inhibitor. Relapse of cancer or mortality of the patient as endpoints of the treatment can be predicted with a high degree of specificity and sensitivity.

The invention claimed is:

1. A method for diagnosis and treatment of ovarian cancer, comprising the steps of:
   (a) measuring the level of antibodies against epidermal growth factor receptor (EGFR) (anti-EGFR antibodies) in a sample from a subject to be diagnosed, wherein the anti-EGFR antibodies bind to EGFR identified as SEQ ID NO:1;
   (b) comparing the measured level of anti-EGFR antibodies in the sample to a control level derived from subjects without cancer;
   wherein a decreased level of anti-EGFR antibodies in the sample from the subject to be diagnosed as compared to the control level is indicative for ovarian cancer in the subject; and
   (c) administering, to the subject diagnosed with ovarian cancer, a drug that is selected from a group consisting of panitumumab, cetuximab, zalutumumab, nimotuzumab, matuzumab, gefitinib, erlotinib, lapatinib, vandetanib, and trastuzumab.

2. The method of claim 1, wherein a level of less than 0.9 fold of the natural log (ln) of the mean value as compared to the control level from subjects without cancer is indicative of ovarian cancer.

3. The method of claim 1, wherein a level of anti-EGFR antibodies below 50 units/ml is indicative of ovarian cancer.

4. The method of claim 1, wherein the anti-EGFR antibody is detected in an immunoassay.

5. The method of claim 4, wherein the immunoassay is selected from the group consisting of immunoprecipitation, enzyme immunoassay (EIA), radioimmunoassay (MA), enzyme-linked immunosorbent assay (ELISA), fluorescent immunoassay, a chemiluminescent assay, an agglutination assay, nephelometric assay, turbidimetric assay, a Western Blot, a competitive immunoassay, a noncompetitive immunoassay, a homogeneous immunoassay, a heterogeneous immunoassay, a bioassay and a reporter assay.

6. The method of claim 1, wherein the sample is serum or plasma.

7. The method of claim 1 wherein determining the level of anti-EGFR antibodies comprises the steps of:
   (a) contacting the sample with epidermal growth factor receptor (EGFR) or an antigenic peptide fragment thereof under conditions allowing for the formation of a complex between anti-EGFR antibodies with EGFR or a peptide fragment thereof; and
   (b) detecting the complex.

8. The method of claim 7, wherein the EGFR or the peptide fragment thereof is immobilized on a surface.

9. The method of claim 7, wherein the complex is detected using a secondary antibody against the Fc portion of the anti-EGFR antibody.

10. The method of claim 9, wherein the anti-EGFR antibody is an IgG-antibody and the secondary antibody is an anti-IgG antibody.

11. The method of claim 10, wherein the secondary antibody is labeled with a detectable marker.

12. The method of claim 1, further comprising detecting a presence of one or more markers for cancer in the sample.

13. A method for diagnosis and treatment of ovarian cancer, comprising the steps of:
  (a) measuring the level of antibodies against epidermal growth receptor (EGFR) (anti-EGFR antibodies) in a sample from a subject to be diagnosed, wherein the anti-EGFR antibodies bind to EGFR identified as SEQ ID NO:1;
  (b) comparing the measured level of anti-EGFR antibodies in the sample to a control level derived from subjects without cancer;
  wherein a decreased level of anti-EGFR antibodies in the sample from the subject to be diagnosed as compared to the control level is indicative for ovarian cancer in the subject; and
  (c) administering, to the subject with a decreased level of anti-EGFR antibodies as compared to the control level derived from subjects without cancer, a drug that is selected from a group consisting of panitumumab, cetuximab, zalutumumab, nimotuzumab, matuzumab, gefitinib, erlotinib, lapatinib, vandetanib, and trastuzumab.

* * * * *